United States Patent
Spatz et al.

(10) Patent No.: US 11,389,408 B2
(45) Date of Patent: Jul. 19, 2022

(54) METHOD FOR PREPARING A FUNCTIONAL SYNTHETIC CELL IN FORM OF A GIANT UNILAMELLAR VESICLE

(71) Applicant: Max-Planck-Gesellschaft zur Förderung der Wissenschaften E.V., Munich (DE)

(72) Inventors: Joachim P. Spatz, Stuttgart (DE); Lucia T. Benk, Stuttgart (DE); Johannes Patrick Frohnmayer, Stuttgart (DE); Barbara Haller, Stuttgart (DE); Jan-Willi Janiesch, Heidelberg (DE); Yilia Plazman, Stuttgart (DE); Marian Weiss, Heidelberg (DE)

(*) Notice: Subject to any disclaimer, the term of this patent is extended or adjusted under 35 U.S.C. 154(b) by 0 days.

(21) Appl. No.: 16/623,363

(22) PCT Filed: Jun. 6, 2018

(86) PCT No.: PCT/EP2018/064927
§ 371 (c)(1),
(2) Date: Dec. 16, 2019

(87) PCT Pub. No.: WO2018/228894
PCT Pub. Date: Dec. 20, 2018

(65) Prior Publication Data
US 2020/0170949 A1    Jun. 4, 2020

(30) Foreign Application Priority Data
Jun. 16, 2017    (EP) .................................... 17176357

(51) Int. Cl.
*A61K 9/127*    (2006.01)
(52) U.S. Cl.
CPC .......... *A61K 9/1277* (2013.01); *A61K 9/1273* (2013.01)

(58) Field of Classification Search
CPC .. A61K 9/1277; A61K 9/1273; A61K 9/1271; A61K 9/0019; A61K 47/34; A61K 9/1075
See application file for complete search history.

(56) References Cited

U.S. PATENT DOCUMENTS

| | | | |
|---|---|---|---|
| 7,803,405 B2 * | 9/2010 | Keating | A61K 47/6901 424/490 |
| 2002/0041895 A1 * | 4/2002 | Gregoriadis | A61K 9/127 424/450 |

(Continued)

FOREIGN PATENT DOCUMENTS

| | | |
|---|---|---|
| WO | 2004/033662 A2 | 4/2004 |
| WO | 2008/154500 A1 | 12/2008 |

OTHER PUBLICATIONS

Bershteyn, A., et al in Royal Society of Chemistry, Soft Matter, vol. 4, pp. 1787-1791, 2008.*

(Continued)

*Primary Examiner* — Gollamudi S Kishore
(74) *Attorney, Agent, or Firm* — Ryder, Mazzeo & Konieczny LLC; Joseph M. Konieczny, Sr.

(57) ABSTRACT

The present invention relates to a method for preparing a protocell in form of a giant unilamellar vesicle, which comprises the following steps: a) providing a water-based droplet encapsulated by an outer polymer shell, which borders the inner space of the droplet, wherein the droplet has a maximum dimension of 0.5 μm to 1,000 μm, wherein the inner space of the droplet contains at least one lipid, b) transforming the lipid content of the droplet into a lipid bilayer which is arranged at and covers the inner surface of the polymer shell and oil phase in order to form a polymer shell-stabilized giant unilamellar vesicle, c) optionally incorporating one or more proteins and/or nuclei into the polymer shell-stabilized giant unilamellar vesicle provided in step b) and d) optionally removing the polymer shell and (Continued)

oil phase from the polymer shell-stabilized giant unilamellar vesicle and optionally transferring it from the oil to the water phase.

18 Claims, 8 Drawing Sheets

(56) References Cited

U.S. PATENT DOCUMENTS

| | | | |
|---|---|---|---|
| 2005/0152963 A1* | 7/2005 | Huwyler | A61K 47/6849 424/450 |
| 2006/0002994 A1* | 1/2006 | Thomas | A61K 9/1272 424/450 |
| 2008/0279922 A1* | 11/2008 | Zalipsky | A61K 47/543 424/450 |
| 2014/0086983 A1* | 3/2014 | Javeri | A61P 7/06 424/450 |
| 2014/0363490 A1 | 12/2014 | Lo et al. | |
| 2015/0050330 A1* | 2/2015 | Lee | A61K 9/1271 424/450 |
| 2015/0104500 A1* | 4/2015 | Markham | A61P 33/06 424/450 |
| 2016/0194368 A1* | 7/2016 | Hoge | C07K 14/535 424/450 |
| 2017/0028365 A1* | 2/2017 | Link | C40B 50/08 |
| 2017/0121756 A1* | 5/2017 | Abate | C12Q 1/686 |

OTHER PUBLICATIONS

Klibanov, A.L., et al in FEBS, vol. 268, # 1, pp. 235-237, 1990.*
Akashi, K et al in Biophysical Journal, vol. 74, pp. 2973-2982, 1998.*
Hannah Stein et al., "Production of Isolated Giant Unilamellar Vesicles under High Salt Concentrations", Frontiers in Physiology, www.frontiersin.org, vol. 8, article 63, Feb. 13, 2017.
Marian Weiss et al., "Sequential bottom-up assembly of mechanically stabilized synthetic cells by microfluids", Nature Materials, www.nature.com/naturematerials, vol. 17, Oct. 16, 2017.
PCT International Search Report and Written Opinion, PCT/EP2018/064927, dated Jul. 25, 2018.

* cited by examiner

Fig. 7
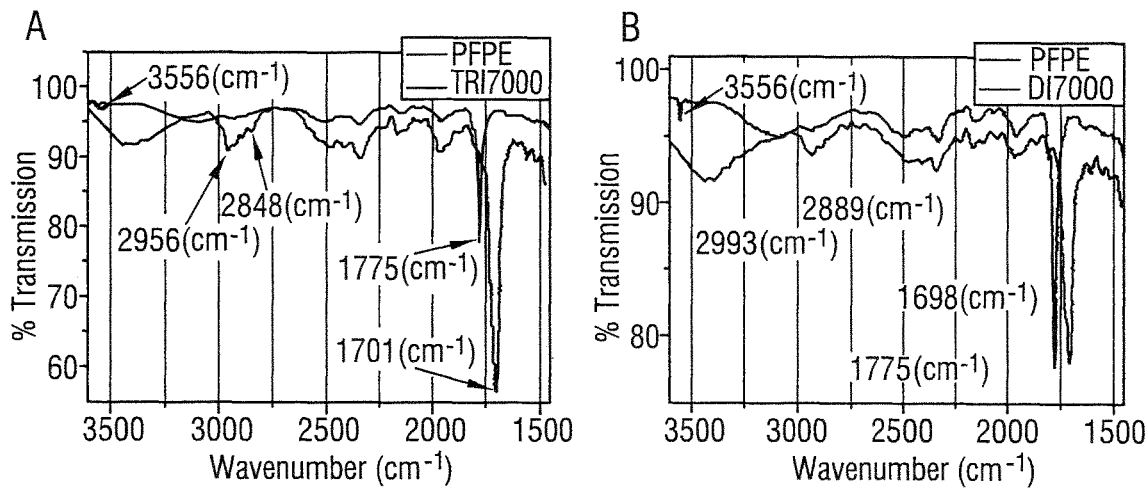
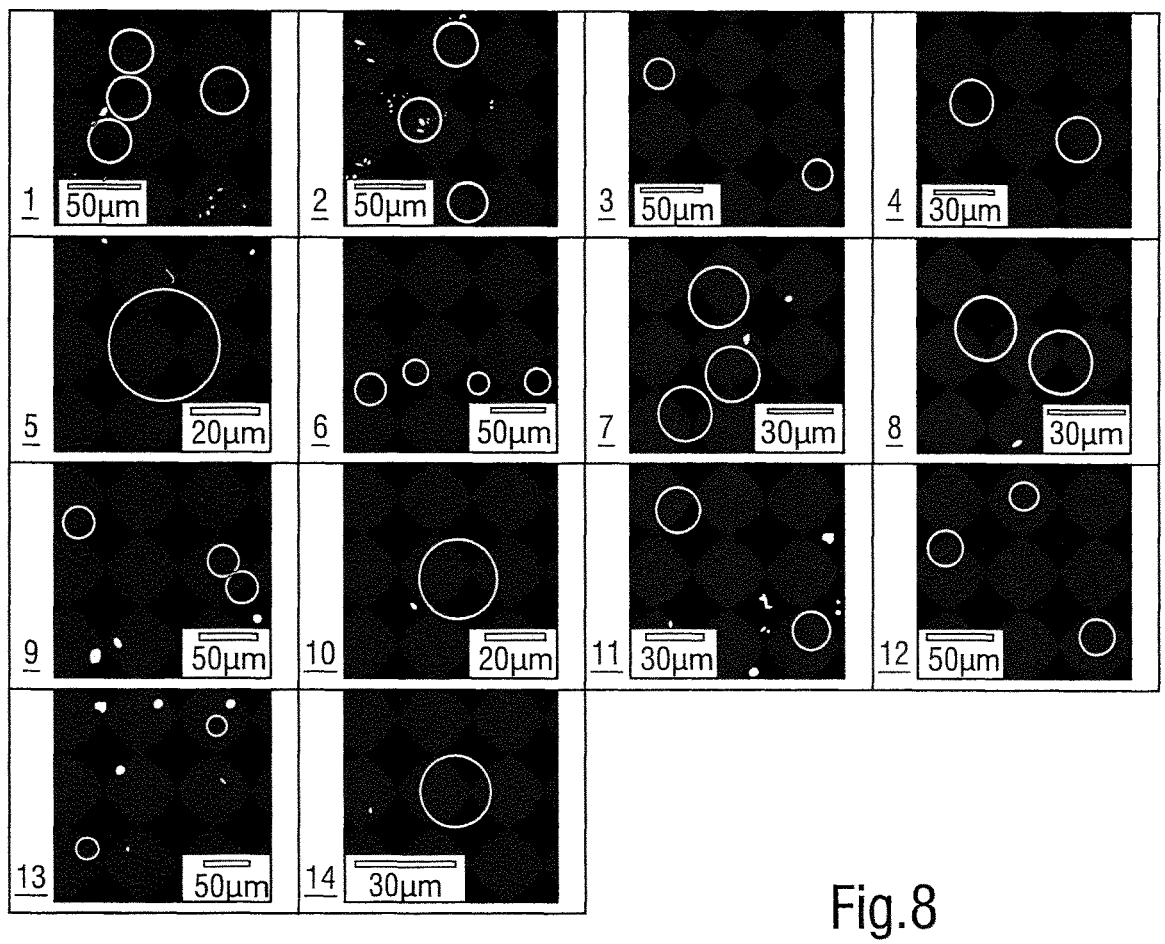
Fig. 8

Fig.13
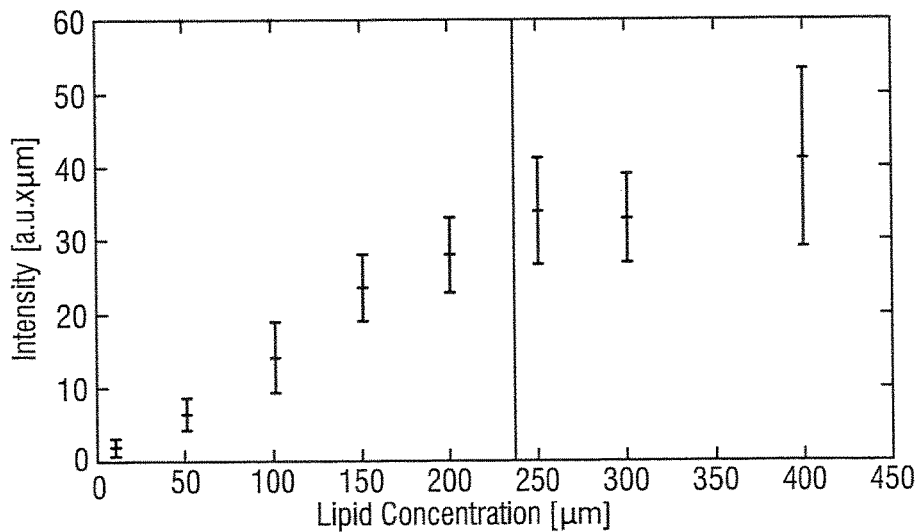
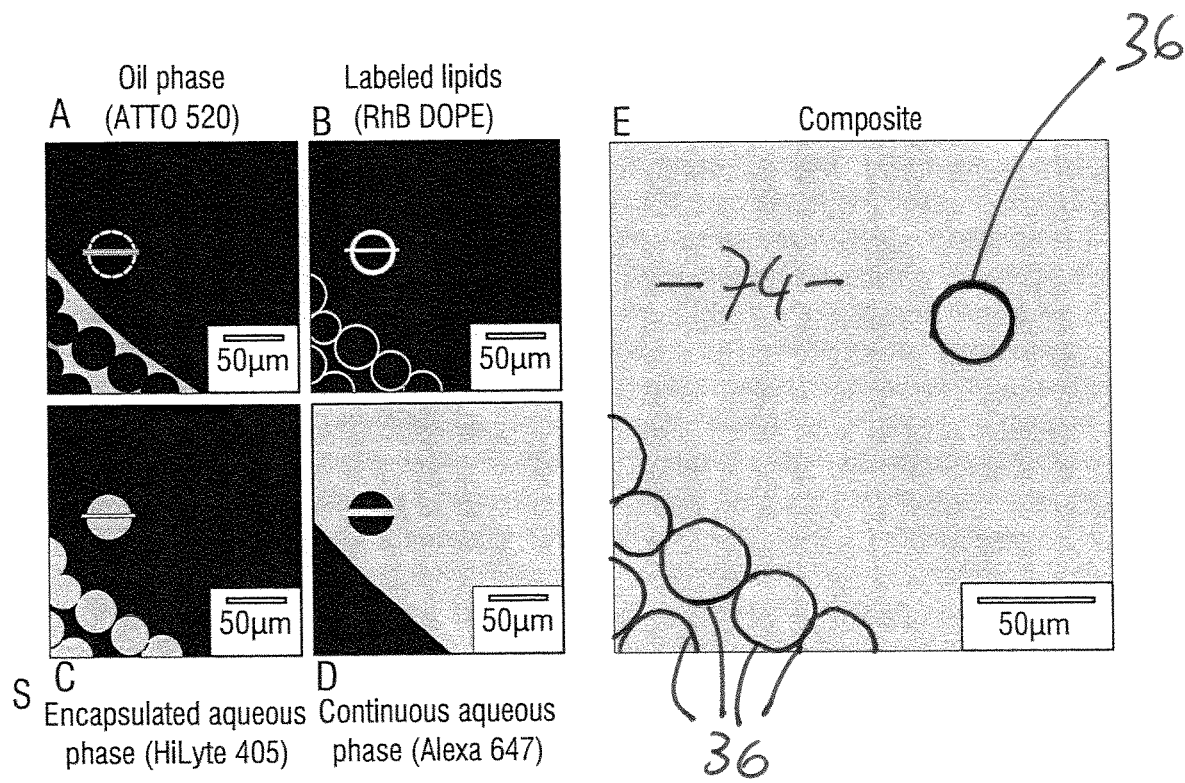
A Oil phase (ATTO 520)
B Labeled lipids (RhB DOPE)
C Encapsulated aqueous phase (HiLyte 405)
D Continuous aqueous phase (Alexa 647)
E Composite
Fig.14

METHOD FOR PREPARING A FUNCTIONAL SYNTHETIC CELL IN FORM OF A GIANT UNILAMELLAR VESICLE

The present invention relates to a method for preparing a synthetic cell in form of a giant unilamellar vesicle as well as to a synthetic cell obtainable with this process. In the following, synthetic cell is named protocell only.

The formation of lipid membrane-based compartments is one of the distinguishing features of eukaryotic cells in contrast to prokaryotic cells. Compartments provide physical and chemical barriers that prevent the uncontrolled diffusion of molecular components to and from the surrounding environment, thereby allowing independent and self-contained metabolic, signaling or synthesizing activities. Moreover, biological membranes allow for chemically selective intra- and intercellular material transport and signal transduction by various transmembrane proteins, such as ion channels and receptors. Therefore, mechanically and chemically well-defined and well-controlled compartments are essential elements for developing and processing life. In the context of synthetic biology, protocells are synthetic, biomolecule-containing, lipid-based compartments. These compartments can either be small unilamellar vesicles (which are abbreviated as SUV), large unilamellar vesicles (which are abbreviated as LUV) or giant unilamellar vesicles (which are abbreviated as GUV). Small unilamellar vesicles, large unilamellar vesicles and giant unilamellar vesicles are usually spherical with a diameter of typically 25 to 50 nm for small unilamellar vesicles, with a diameter of typically more than 50 to 1,000 nm for large unilamellar vesicles and with a diameter of typically 1 to 1,000 µm for giant unilamellar vesicles. However, the chemical and mechanical instabilities of unsaturated fatty acids under high ionic strength conditions, especially multivalent cations, and their sensitivity to pH changes are considered to be the main challenges in utilizing protocells for synthetic biology. In addition, inserting molecules into protocells represents a particular challenge given their impermeability and mechanical instability.

Electroformation is a method, which relies on applying a low voltage, typically alternating electric field during hydration of dried lipid films in aqueous solution. More specifically, in one known variant of this technique giant unilamellar vesicles are formed in channels sandwiched between glass slides coated with indium tin oxide electrodes by applying an alternative current. However, low GUV yield in physiological buffer solutions, heterogeneous in GUV's lipid composition and strong limitations to small amount of charged lipids (<10%) remain the major drawbacks of electroformation method for GUVs production. In contrast to this, microfluidic phase transfer methods comprise that in a circuit lipid-stabilized water-in-oil droplets, which are generated by flow focusing at low capillary number, are presented to a parallel extravesicular aqueous flow at high capillary number. The droplets are physically transferred through the lipid-stabilized oil/water interface upon reaching a micforabricated post, collecting a second outer coat of lipids to complete the vesicle bilayer. The advantage of microfluidic methods is that GUVs can be produced at high-throughput with the control over the uniform compartment size. Moreover, the choice of membrane composition and buffer conditions is more flexible compared to the electroformation method. However, independently from the production processes, the manipulability remains limited as the so obtained GUVs are chemically and particularly mechanically instable mainly on account of the chemical and mechanical instabilities of unsaturated fatty acids and phospholipids under high ionic strength conditions, so that they cannot be loaded additionally or sequentially with proteins, in particular transmembrane proteins and cytoskeleton proteins, for example by a pico-injection technology.

As alternative compartments to protocells in form of giant unilamellar vesicles polymersomes are known, which are made from amphiphilic block copolymers. They enclose and are typically surrounded by an aqueous solution. Some polymersomes can be engineered with transmembrane proteins or synthetic channel molecules that enable certain chemicals to pass the polymer membrane, since they are both chemically and mechanically more stable than protocells in form of giant unilamellar vesicles and are adjustable to certain environments and functionalities. In contrast to giant unilamellar vesicles, however, where the manipulation of chemical and physical properties bears limitations, the thickness, bending and stretching moduli of the polymeric membrane is tuned by changing the block-copolymer molecular properties. However, the encapsulation of biomolecules and further manipulation of traditional water-in-water polymersomes still represent challenges. The uncontrolled permeability of the polymersomes and a lack of technologies, which allow for the precise and efficient delivery of different biological components, are the main drawbacks.

Yang et al. describe in Nature Chemistry 2016, pages 476 to 483 a method to generate highly monodispersed sub-100-nm unilamellar vesicles, where liposome self-assembly is nucleated and confined inside rigid DNA nanotemplates. More specifically, a small DNA ring is formed, before a liposome is formed within the DNA ring. These sub-100-nm unilamellar vesicles are, however, mechanically instable and cannot be loaded with proteins by injection, such as by a pico-injection technology because of their small size. Moreover, DNA rings may be hardly formed in a size, which would be necessary to encapsulate giant unilamellar vesicles.

In view of the above, the object underlying the present invention is to provide a method for the spatially and temporally controlled assembly of biological processes within an improved protocell in form of a giant unilamellar vesicle. Wherein the giant unilamellar vesicle is chemically as well as mechanically stabilized so that it can be loaded sequentially with different proteins and molecules, such as transmembrane proteins and cytoskeleton, for example by using pico-injection technology. Moreover, the method shall be easy and time-efficient and shall allow a high throughput production of giant unilamellar vesicles.

In accordance with the present invention, this object is satisfied by providing a method for preparing a protocell in form of a giant unilamellar vesicle, which comprises the following steps:

a) providing a water-based droplet encapsulated by an outer polymer shell, which borders the inner space of the droplet, wherein the droplet has a maximum dimension of 0.5 µm to 1,000 µm, wherein the inner space of the droplet contains at least one lipid, b) transforming the lipid content of the droplet into a lipid bilayer which is arranged at and covers the inner surface of the polymer shell in order to form a polymer shell-stabilized giant unilamellar vesicle, c) optionally incorporating one or more proteins and/or nuclei into the polymer shell-stabilized giant unilamellar vesicle provided in step b) and d) optionally removing the polymer shell and oil phase from the polymer shell-stabilized giant unilamellar vesicle.

This solution bases on the surprising finding that by providing a water-based droplet encapsulated by an outer polymer shell, which borders the inner space of the droplet, wherein the droplet has a maximum dimension of 0.5 µm to 1,000 µm, wherein the inner space of the droplet contains at least one lipid, and by transforming the lipid content of the droplet into a lipid bilayer which is arranged at and covers the inner surface of the polymer shell, a polymer shell-stabilized giant unilamellar vesicle is obtained, which is chemically as well as mechanically notably stabilized. In particular in the preferred embodiment described below, in which during step a) a water-in-oil dispersion is provided, in which the droplet with the outer polymer shell is dispersed in an oil-phase, wherein in the inner space of the droplet an aqueous-based phase comprising the at least one lipid is contained, the chemical as well as mechanical stability of the polymer shell-stabilized giant unilamellar vesicle is drastically improved in comparison to the respective giant unilamellar vesicles known in the prior art. On account of this high chemical and particularly high mechanical stability, the polymer shell-stabilized giant unilamellar vesicle can be easily treated with an injection technology, such as pico-injection technology, and thus can be easily loaded with proteins, such as transmembrane proteins and cytoskeleton proteins. Afterwards, the polymer shell may be removed from the giant unilamellar vesicle. Furthermore, the proposed method is easy and time-efficient. In addition, the method in accordance with the present invention allows a high-throughput production of giant unilamellar vesicles, namely the production of typically 1,000 giant unilamellar vesicles per second or more. Consequently, the method in accordance with the present invention can be performed by high-throughput microfluidics.

All in all, the droplet-sized and highly stable and therefore manipulable cell-like compartments, i.e. protocells, of a defined size obtainable with the method in accordance with the present invention are ideal for modelling and investigating biophysical and biochemical processes within a well-defined microenvironment. The enhanced stability enables the sequential loading of these compartments with biomolecules by pico-injection microfluidics and thus allows a bottom-up assembly of a compartment with contents that would not self-assemble to full functionality when simply mixed together, namely lipids, purified transmembrane proteins and cytoskeleton proteins. Following the assembly, the polymer shell as well as optionally the stabilizing oil phase can be easily entirely removed so as to release self-supporting protocells containing for instance functional cytoskeleton and adhesion proteins to aqueous phase and enable them to interact with physiological relevant living cells, matrices and proteins.

Giant unilamellar vesicles are according to the present invention unilamellar vesicles, which are preferably, but not necessarily spherical, with a maximum dimension of 0.5 µm to 1,000 µm. Preferably, the giant unilamellar vesicle is spherical and has thus an outer diameter of 0.5 µm to 1,000 µm.

In accordance with the present invention, a droplet is a small volume of liquid, irrespective of its form. Preferably, the droplet is at least substantially ellipsoidal or at least substantially spherical. More preferably, the droplet provided in step a) is spherical and has an outer diameter of 0.5 to 1,000 µm, even more preferably of 10 to 1200 µm and most preferably of 20 to 60 µm. This allows to obtain spherical giant unilamellar vesicle with a cell-like size.

In addition, in accordance with the present invention, a water-based droplet is a droplet, which contains water or a dispersion of any substance in water. Also, a water-based droplet is a droplet, which consists of water or of a dispersion of any substance in water. More specifically, a water-based droplet in the sense of the present invention is a droplet which is composed of water including salts and the at least one lipid.

As indicated above, according to a particular preferred embodiment of the present invention, in step a) a dispersion is provided, in which the droplet is dispersed in an oil-phase, wherein an aqueous phase comprising the at least one lipid is contained in the inner space of the droplet. In this embodiment, the giant unilamellar vesicle is not only stabilized by the polymer shell, but also by the outer oil phase so that the chemical as well as mechanical stability of the polymer shell-stabilized giant unilamellar vesicle is drastically improved in comparison to the respective giant unilamellar vesicles known in the prior art. The inventors have shown that the continuous oil phase comprising the amphiphilic copolymers plays an important role not only in the stable separation of the droplets and in preserving its content, but also in the combinatorial delivery of biological materials exclusively into the droplets by means of picoinjection technology. In this embodiment, during step d) preferably the giant unilamellar vesicle, from which the polymer shell has been removed, is transferred from the oil to the water phase.

In order to allow a good dispersion of the droplet in the oil phase and in order to allow a good dispersion of the lipid containing aqueous phase within the polymer shell of the droplet, it is proposed in a further development of the idea of the present invention that the polymer shell of the droplet is made of an amphiphilic copolymer with a lipophilic end arranged at the outer side and a hydrophilic end arranged at the inner side of the polymer shell.

This may be achieved by forming the polymer shell of the droplet of a diblock copolymer, a triblock copolymer or a statistic copolymer.

Good results are particularly obtained, if the polymer shell of the droplet is made of a block copolymer comprising a lipophilic or a hydrophobic block arranged at the outer side and a hydrophilic block arranged at the inner side of the polymer shell. The lipophilic or hydrophobic block may be, but is not restricted to members, e.g. selected from the group consisting of perfluorinated polymers, such as perfluorinated polyethers, polystyrene or poly(olefin oxides), such as poly (propylene oxide), whereas the hydrophilic block may be selected e.g. from polyether glycols, polyetheramine, polyacrylate acid, polymethylacrylate acid or poly[poly(ethylene glycol) methyl ether methacrylate].

Likewise, good results are obtained, if the polymer shell of the droplet is made of a triblock copolymer comprising two hydrophobic perfluorinated polymer end blocks and therebetween a hydrophilic polyether glycol block, wherein the triblock copolymer is folded so that the hydrophobic perfluorinated polymer blocks are arranged at the outer side and that the hydrophilic polyether glycol block is arranged at the inner side of the polymer shell. Examples for the lipophilic or hydrophobic blocks and the hydrophilic blocks are the same as those mentioned above.

Preferably, the perfluorinated polymer block is a perfluorinated polyether block (PFPE) and more preferably a perfluorinated polyether block having a weight average molecular weight of 1,000 to 10,000 g/mol. Likewise preferably, the polyether glycol (PEG) and polyetheramine (JEFFAMINE) blocks have preferably a weight average molecular weight of 100 to 10,000 g/mol. More specifically, suitable examples for the respective copolymers are PFPE-carboxylic acid (Krytox, MW 2500 or 7000 g/mol) and suitable examples for the respective diblock copolymers are PFPE(7000 g/mol)-PEG(1400 g/mol), PFPE(7000 g/mol)-PEG(600 g/mol), PFPE(2500 g/mol)-PEG(600 g/mol), PFPE(4000 g/mol)-PEG(600 g/mol), PFPE(4000 g/mol)-PEG(1400 g/mol), PFPE(2000 g/mol)-PEG(600 g/mol), PFPE(7000 g/mol)-JEFFAMINE(600 g/mol), PFPE(7000 g/mol)-JEFFAMINE (900 g/mol), PFPE(2500 g/mol)-JEFFAMINE (600 g/mol), PFPE(2500 g/mol)-JEFFAMINE(900 g/mol), PFPE(4000 g/mol)-JEFFAMINE(900 g/mol), PFPE(2500 g/mol)-JEFFAMINE(600 g/mol), PFPE(2000 g/mol)-JEFFAMINE (600 g/mol), PFPE(2000 g/mol)-JEFFAMINE (900 g/mol) and suitable examples for the respective triblock copolymers are PFPE(7000 g/mol)-PEG(1400 g/mol)-PFPE (7000 g/mol), PFPE(7000 g/mol)-PEG(600 g/mol)-PFPE (7000 g/mol), PFPE(4000 g/mol)-PEG(1400 g/mol)-PFPE (4000 g/mol) PFPE(2500 g/mol)-PEG(600 g/mol)-PFPE (2500 g/mol), PFPE(2000 g/mol)-PEG(600 g/mol)-PFPE (2000 g/mol), PFPE(7000 g/mol)-JEFFAMINE(900 g/mol)-PFPE(7000 g/mol) PFPE(7000 g/mol)-JEFFAMINE(600 g/mol)-PFPE(7000 g/mol), PFPE(4000 g/mol)-JEFFAMINE(900 g/mol)-PFPE(4000 g/mol), PFPE(4000 g/mol)-JEFFAMINE(600 g/mol)-PFPE(4000 g/mol), PFPE(2500 g/mol)-JEFFAMINE(900 g/mol)-PFPE(2500 g/mol), PFPE (2500 g/mol)-JEFFAMINE(600 g/mol)-PFPE(2500 g/mol), PFPE(2000 g/mol)-JEFFAMINE(900 g/mol)-PFPE(2000 g/mol) and PFPE(2000 g/mol)-JEFFAMINE(600 g/mol)-PFPE(2000 g/mol). The molecular weight is determined with gel permeation chromatography using a polystyrene standard.

According to a further preferred embodiment of the present invention, gold nanoparticles are attached to the hydrophilic end of the copolymer forming the polymer shell. The gold nanoparticles may be used as anchors to immobilize protein or peptides, such as arginine-glycine-aspartic acid (RGD)-peptides, at the inner surface of the polymer shell.

The present invention is not particularly limited concerning the chemical nature of the at least one lipid contained in the inner space of the droplet with an outer polymer shell, as long as it is able to form a lipid bilayer. Good results are in particular achieved with phospholipid and in particular with a lipid being selected from the group consisting of phosphocholine, phosphocholine derivatives, phosphoethanolamine, phosphoethanolamine derivatives, phosphatidylcholine, phosphatidylcholine derivatives, phosphatidylglycerol, phosphatidylglycerol derivatives and arbitrary combinations of two or more of the aforementioned lipids. Specific suitable examples for lipids are those selected from the group consisting of 1,2-dioleoyl-sn-glycero-3-phosphocholine (DOPC), 1,2-dioleoyl-sn-glycero-3-phosphoethanolamine (DOPE), 1,2-dioleoyl-sn-glycero-3-phospho-L-serine (DOPS), 1,2-di-(9Z-octadecenoyl)-sn-glycero-3-phospho-(1'-rac-glycerol) (DOPG), 1,2-dioleoyl-3-trimethylammonium-propane (DOTAP), 1,2-dioleoyl-sn-glycero-3-[(N-(5-amino-1-carboxypentyl)iminodiacetic acid) succinyl] (DGS-NTA), 1,2-dioleoyl-sn-glycero-3-phosphoethanolamine-N-(lissamine rhodamine B sulfonyl) (RhB DOPE), 1-palmitoyl-2-hydroxy-sn-glycero-3-phosphate, L-α-phosphatidylcholine, L-α-phosphatidylglycerol and arbitrary combinations of two or more of the aforementioned lipids.

Concerning the technique for incorporating the at least one lipid into the inner space bordered by the polymer shell of the droplet, the present invention is not limited. For example, any suitable microfluidics or other techniques for water-in-oil emulsion may be used.

In accordance with one particular preferred embodiment of the present invention, the at least one lipid is incorporated in the inner space of the droplet during step a) by droplet generation in a flow-focusing microfluidic device. In this technique, which is described in more detail below in connection with FIG. 2, two-phases, namely the continuous phase and the dispersed phase, meet at a flow-focusing junction. The flow-focusing junction consists of three inlet channels converging into a main channel or outlet channel, respectively, via a narrow orifice. For example, two of three inlet channels are arranged in the vertical direction, wherein both vertical inlet channels converge at the flow-focusing junction, one coming from above and one coming from below the flow-focusing junction. Furthermore, the third inlet channel is arranged in the horizontal direction and meets the other two inlet channels at the flow-focusing junction coming from the left side. The main channel or outlet channel, respectively, is also arranged in the horizontal direction and starts with its narrow orifice on the side opposite the terminal end of the horizontal inlet channel. During the operation, the continuous oil phase comprising the amphiphilic copolymer(s) (which later form the polymer shell) dispersed or dissolved in oil, flows through the two vertical inlet channels, wherein both continuous oil phase partial streams converge at the flow-focusing junction. The dispersed aqueous phase including the lipid(s) flows through the horizontal inlet channel and is squeezed at the flow-focusing junction by the oil-phase flowing through the two vertical inlet channels. Both phases pass through the small orifice that is located downstream the three inlet channels, wherein the stream of the dispersed phase becomes narrow and breaks into droplets of the lipid containing aqueous phase, wherein the droplets are covered by the amphiphilic copolymer(s) thus forming a polymer shell, with the lipophilic or hydrophobic end of the copolymer being oriented at the outer shell side towards the continuous oil phase and the hydrophilic end of the copolymer being oriented at the inner shell side towards the dispersed, lipid containing aqueous phase. The droplet size can be adjusted by the flow rates of the two phases, by the flow rate ratio and by the channel geometries.

Alternatively, the at least one lipid may be incorporated into the inner space of the droplet during step a) by other droplet generation techniques for example comprising the merging of two phases in a flow microfluidics technique. For instance, the continuous oil phase comprising the amphiphilic copolymer(s) later forming the polymer shell dispersed or dissolved in oil, and the dispersed aqueous phase including the lipid(s) may converge at a T-junction.

In accordance with an alternative preferred embodiment of the present invention, the at least one lipid is incorporated into the inner space of the droplet during step b) by electro-microfluidics making use of an injector, which is preferably a pico-injector. In this technique, which is described in more detail below in connection with FIG. 4, a dispersion of droplets is flown through a channel. On one side of the channel two electrodes are arranged, which apply an alternating electrical potential on the channel, whereas on the other side of the channel a pico-injector is arranged, through which liquid may be injected into the channel. During operation, an alternating electric potential, such as of 250 V and 1 kHz, is applied, which reduces the stability of the polymer shell, whereby the incorporation of the lipid containing aqueous liquid provided by the pico-injector into the droplet is enabled.

The liquid(s) may be included in the inner space of the droplet as an aqueous dispersion of small, large or giant unilamellar lipid-vesicles. However, it is preferred if the lipid(s) are included in the inner space of the droplet as small or large well-dispersed unilamellar vesicles, in order to facilitate the transformation into a bilayer on the inner droplet periphery in step b).

Good results are obtained with this regard, when the at least one lipid is incorporated into the inner space of the droplet during step a) in form of small or large unilamellar lipid-vesicles, wherein the large unilamellar lipid-vesicles have been e.g. formed by dissolving the lipid(s) in a solvent, such as chloroform, drying the so obtained mixture under inert gas atmosphere, resuspending the dried lipid in an aqueous buffer, vortexing the mixture and homogenizing the vesicle size by extruding the so obtained mixture through a filter. For instance, the filter may be a polycarbonate filter with a pore size of 50 nm. Alternatively, in the case of proteoliposomes, the large unilamellar lipid-vesicles may be formed through detergent removal.

Still alternatively, the at least one lipid may be incorporated into the inner space of the droplet during step a) in form of small, large or giant unilamellar lipid-vesicles, which have been formed by an electroforming process, preferably by a process comprising the steps of dissolving the lipid(s) in a solvent, such chloroform, of spreading the so obtained mixture onto two indium oxide coated glasses, evaporating the solvent, filling the space between the two glasses with water and applying an alternative electrical potential of 1 to 100 Hz at 0.1 to 10 Volt for 0.1 to 10 hours.

In order to transform the lipid content of the droplet in step b) of the method in accordance with the present invention into a lipid bilayer which is arranged at and covers the inner surface of the polymer shell so as to form a polymer shell stabilized giant unilamellar vesicle, an electrostatic interaction between the small and large unilamellar lipid vesicles and the inner surface of the polymer shell is required. This may be achieved by forming the polymer shell of the droplet of a negatively charged block copolymers. Good results are particularly obtained if the polymer shell of the droplet is made of statistic copolymer consisting of PEG-based diblock and triblock copolymers or PEG- or JEFFAMINE-based triblock and PFPE-carboxylic acid copolymers. The negatively charged inner surface of the polymer shell attracts earth alkaline ions, and in turn, promotes formation stabilized giant unilamellar vesicle by adhesion and rapturing of neutral or negatively charged small or large unilamellar vesicles. The inventors have shown that adjustment of the concentration to a suitable value of earth alkaline ions, more preferably of calcium ions or magnesium ions and most preferably of magnesium ions, is required. In particular, the adjustment of the concentration of magnesium ions to a suitable value is effective for transforming the lipid content of the droplet during step b) into a lipid bilayer. Preferably, the lipid content of the droplet is transformed during step b) into a lipid bilayer by adjusting the concentration of ions, in particular magnesium ions, within the inner space of the droplet and/or applying electric fields. Particular advantageous is to transform the lipid content of the droplet during step b) into a lipid bilayer by adjusting the concentration of magnesium ions to a value of 1 to 100 mM, more preferably to a value of 2 to 100 mM, still more preferably to a value of 5 to 50 mM, even more preferably to a value of 5 to 20 mM and most preferably to a value of 8 to 12 mM, such as in particular to about 10 mM. It has been found that such a magnesium ion concentration is most efficient for transforming the lipid content of the droplet in step b) into a lipid bilayer.

According to a further preferred embodiment of the present invention, the concentration of magnesium ions within the inner space of the droplet is adjusted during the droplet formation. More specifically, it is preferred that the at least one lipid is incorporated into the inner space of the droplet during step a) by droplet generation in a flow-focusing microfluidic device, as described above, wherein the lipid containing aqueous phase used therefore has a respective magnesium concentration, i.e. a magnesium ion concentration of preferably 1 to 100 mM, more preferably of 2 to 100 mM, even more preferably of 5 to 50 mM, still more preferably of 5 to 20 mM and most preferably of 8 to 12 mM, such as in particular of about 10 mM. It has been found by the inventors of the present invention that the formation of the lipid bilayer is completed in the case of a magnesium ion concentration of the lipid containing aqueous phase included in the inner space of the droplet of 10 mM within a few seconds, when the lipid(s) are included in the droplet in form of small and large unilamellar lipid-vesicles. In contrast thereto, the formation of the lipid bilayer lasts for about 30 minutes in the case of a magnesium ion concentration of the lipid containing aqueous phase included in the inner space of the droplet of 10 mM, when the lipid(s) are included in the droplet in form giant unilamellar lipid-vesicles. Accordingly, in these embodiments the transformation of the lipid content of the droplet into a lipid bilayer according to step b) starts during conducting step a), wherein the transformation of the lipid content of the droplet into a lipid bilayer according to step b) ends seconds or even dozens of minutes after termination of step a). Thus, in these embodiments step b) actually overlaps in time with step a).

In accordance with an alternative preferred embodiment of the present invention, the concentration of magnesium ions within the inner space of the droplet is adjusted during step b) by electro-microfluidics making use of an injector, which is preferably a pico-injector. The pico-injector may be the same as described above and as shown in FIG. 4. In this embodiment, step b) is performed after step a).

Neutral and negatively charged giant unilamellar vesicles are processed in the above described same manners, whereas positively charged giant unilamellar vesicles are forming also without additions of ions due to direct electrostatic interactions with the negatively charged inner surface of the polymer shell. Alternatively, electric fields may be applied to fuse lipids to giant unilamellar vesicles at the inner interface of polymer droplets.

In accordance with optional step c), one or more proteins may be incorporated into the polymer shell-stabilized giant unilamellar vesicle provided in step b). This optional step is possible, since the polymer shell-stabilized giant unilamellar vesicle provided in step b) is due to the reasons set out above chemically and mechanically notably stable. On account of this reason, it is preferred to actually perform the step c), i.e. to incorporate one or more proteins into the polymer shell-stabilized giant unilamellar vesicle provided in step b). The proteins may be provided in a buffer soluble form or the proteins may be already incorporated into the wall of small protein liposomes thus forming proteoliposomes, i.e. vesicles having preferably at least one lipid bilayer, into which the one or more proteins have been inserted. These protein liposomes fuse with the given giant unilamellar vesicle inside the droplet. For instance, step c) may be performed by incorporating one or more proteins into the polymer shell-stabilized giant unilamellar vesicle provided in step b) by electro-microfluidics making use of an injector, which is preferably a pico-injector. The pico-injector may be the same as described above and as shown in FIG. 4.

More preferably, the one or more proteins are incorporated in this embodiment into the polymer shell-stabilized giant unilamellar vesicle by injecting them with the pico-injector in form of respective proteoliposomes.

For instance, during step c) a transmembrane protein and/or a cytoskeleton protein may be incorporated into the lipid bilayer and/or into the inner space of the polymer shell-stabilized giant unilamellar vesicle. The present invention is not at all limited to the kind of protein incorporated into the polymer shell-stabilized giant unilamellar vesicle. Just exemplarily proteins selected from the group consisting of receptors, ATP-synthase, polymerase, actin, tubulin, anti-bodies, integrins, nuclei as isolated from cells and arbitrary combinations of two or more of the aforementioned proteins and nuclei are mentioned. As actin, G-actin and F-actin may be mentioned. Other proteins, which may be used, are, but are not limited to ribosomes and ribosome-associated proteins, nucleus or nucleus associated proteins, signaling proteins, immunologically relevant proteins, anti-bodies, different ion-pump proteins, adhesion associated proteins and synthetic molecules which link different proteins and molecules with each other.

In accordance with optional step d), the polymer shell and the oil phase are removed from the polymer shell-stabilized giant unilamellar vesicle. Since the polymer shell is not necessary any more after the incorporation of the one or more proteins into the polymer shell-stabilized giant unilamellar vesicle, which requires the mechanical stability effected by the polymer shell, it is actually preferred to perform the step d) so as to obtain a giant unilamellar vesicle. In addition, it is required to disperse the giant unilamellar vesicle after removal of the polymer shell and oil phase in an aqueous phase.

For instance, the polymer shell and the oil phase may be removed from the polymer shell-stabilized giant unilamellar vesicle during step d) by a microfluidic device or by a bulk technique by adding destabilizing molecules. For instance, the removal step may be performed in a microfluidic device shown in FIG. 5 as discussed in further detail below. More specifically, the device comprises a first inlet channel for introducing the polymer shell-stabilized giant unilamellar vesicle and a second inlet channel for introducing a dispersion of polymer shell destabilizing surfactant(s) in oil into the first inlet channel. For this purpose, the first and second inlet channels are connected via a T-junction. Furthermore, downstream the T-junction, passive trapping structures are provided which decelerate the giant unilamellar vesicle. Further downstream, i.e. downstream the passive trapping structures, the first inlet channel merges into a wide perpendicular channel, in which aqueous phase is flowing. Preferably, the total flow is adjusted in the microfluidic device during the operation so as to give the destabilizing surfactant(s) introduced via the second inlet channel sufficient time to destabilize the polymer shell of the polymer shell-stabilized giant unilamellar vesicle in the first inlet channel. In addition, the height of the channels is preferably designed to exceed the diameter of the polymer shell-stabilized giant unilamellar vesicle and the pressure in the inlet channels is preferably adjusted to a maximum of 20 mbar, so as to minimize shear forces within the first inlet channel. As destabilizing surfactant, for instance an oil flow containing 20% by volume perfluoro-1-octanol may be used. The passive trapping structures are provided to decelerate the giant unilamellar vesicle so as to minimize the mechanical impact on the giant unilamellar vesicle at the downstream junction to the wide perpendicular channel, in which the aqueous phase is flowing. Upon contact of the polymer shell-stabilized giant unilamellar vesicle with the aqueous phase at the junction of the first inlet channel and the wide perpendicular channel, in which the aqueous phase is flowing, the giant unilamellar vesicle without polymer shell is released into the aqueous phase.

The removal step may also be performed by means of a bulk technique shown. For the bulk removal approach 100 µl of formed polymer shell-stabilized giant unilamellar vesicles is collected in an Eppendorf tube. Due to the density differences between the fluorinated oil and water, the polymer shell-stabilized giant unilamellar vesicles form a dense layer at the top of the tube. To provide an aqueous phase for polymer shell removal, 100 µl of buffer is added as a one large drop in the center of the polymer shell-stabilized giant unilamellar vesicles layer. To reduce osmotic pressure effect, it is preferable that the buffer ionic content will be identical to the buffer content within the polymer shell-stabilized giant unilamellar vesicles. Following the addition of buffer, an oil containing 20% by volume of perfluoro-1-octanol is gently dripped on top of the buffer drop. After applying the complete volume of destabilizer, the tube is tilted to increase the interface area and slowly rotated about its longitudinal axis. In that conditions the emulsion breakage takes less than five minutes. The aqueous solution containing giant unilamellar vesicles without polymer shell can be carefully removed with a pipette.

A further aspect of the present invention is a protocell in form of a polymer shell-stabilized giant unilamellar vesicle with an outer polymer shell obtainable with a process comprising the aforementioned steps a) and b) and optionally further step c).

That means, the present invention particularly relates to a protocell in form of a polymer shell-stabilized giant unilamellar vesicle comprising an outer polymer shell, which borders an inner space, wherein the giant unilamellar vesicle has a maximum dimension of 0.5 µm to 1,000 µm, and further comprising a lipid bilayer being composed of at least one lipid, wherein the lipid bilayer is arranged at and covers the inner surface of the polymer shell.

Furthermore, the present invention relates to a protocell in form of a giant unilamellar vesicle obtainable with a process comprising the aforementioned steps a), b) and d) and optionally further step c).

Preferably, the protocell in accordance with the present invention comprises a transmembrane protein and/or a cytoskeleton protein in the lipid bilayer and/or in the inner space. For instance, the protein may be selected from the group consisting of integrin, ATP-synthase, G-Actin, tubulin, ribosomes and ribosome-associated proteins, nucleus or nucleus associated proteins, signaling proteins, immunologically relevant proteins, anti-bodies, different ion-pump proteins, adhesion associated proteins and synthetic molecules which link different proteins and molecules with each other and arbitrary combinations of two or more of the aforementioned proteins.

Subsequently, the present invention is described by means of figures, which do, however, not limit the present patent application, wherein.

FIG. 7 shows the FTIR spectra of the reactants and the products of the copolymer synthesis performed in example 1. (A) shows the comparison between the PFPE(7000)-carboxylic acid (20 mM) as a reactant and the PFPE(7000)-PEG(1400)-PFPE(7000) triblock product (20 mM) as described in example 1. (B) shows the comparison between PFPE(7000)carboxylic acid as a reactant (20 mM) and the PFPE(7000)-PEG-OMe(750) diblock product (20 mM) as described example 1.

FIG. 8 shows the vesicles produced in example 2 as summarized in table 1.

Figure 9:
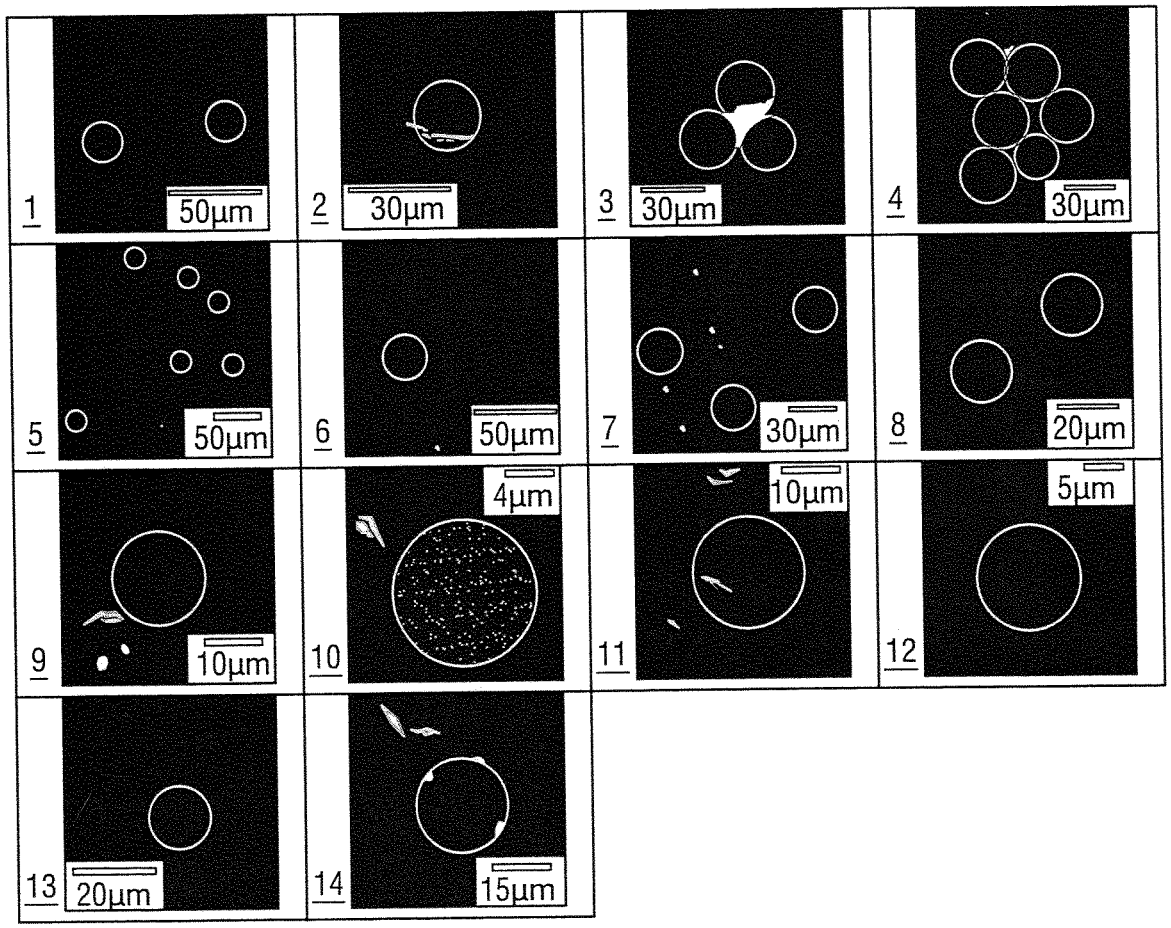

FIG. 9 shows the vesicles produced in example 2 as summarized in table 2.

Figure 10:
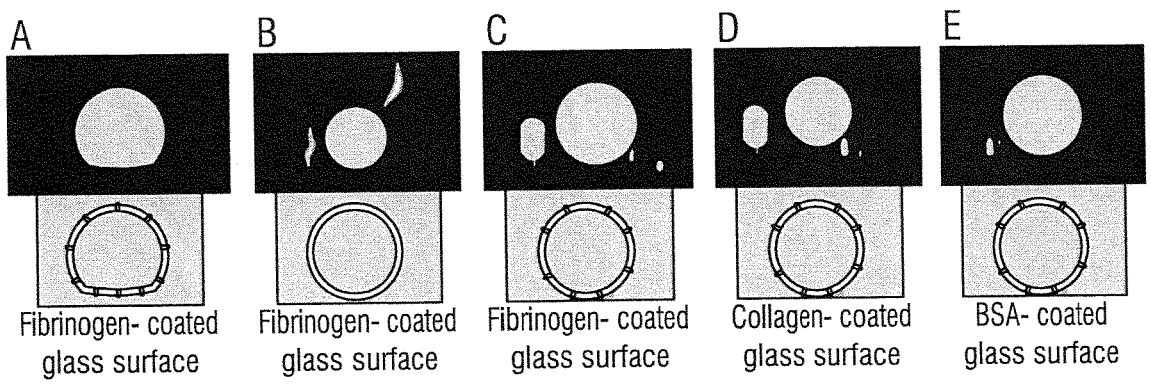

FIG. 10 shows integrin giant unilamellar vesicles after release and in adhesion contact with different matrices in physiologic buffer solution as obtained in example 7.

Figure 11:
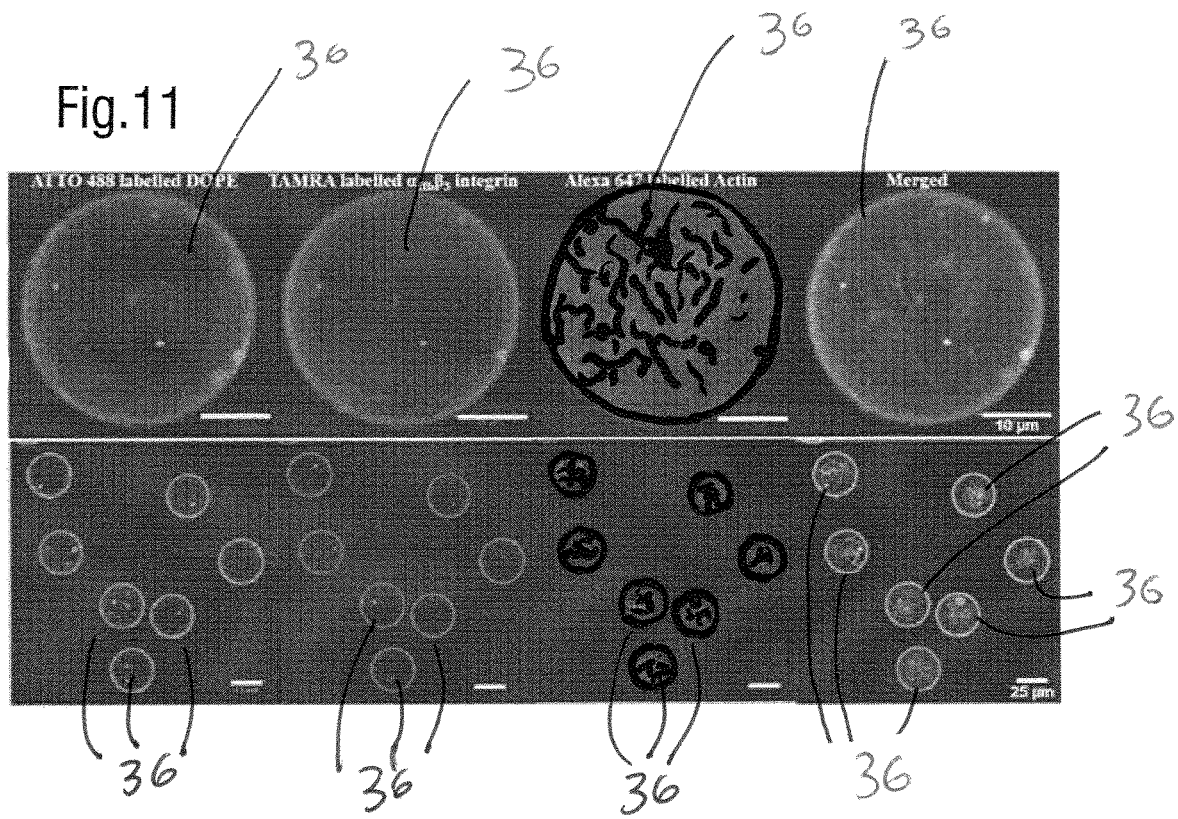

FIG. 11 shows representative fluorescence images of the polymer shell-stabilized giant unilamellar vesicles (1% ATTO 488-labeled DOPE, first panel), the reconstituted TAMRA-labelled αIIbβ3 integrin (second panel), the actin cytoskeleton (1% Alexa Fluor 647-labeled actin, third panel) and the composite fluorescence image of all channels (fourth panel) showing the actin and integrin reconstituted polymer shell-stabilized giant unilamellar vesicles.

Figure 12:
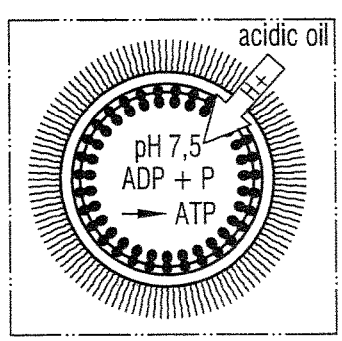
Figure 12:
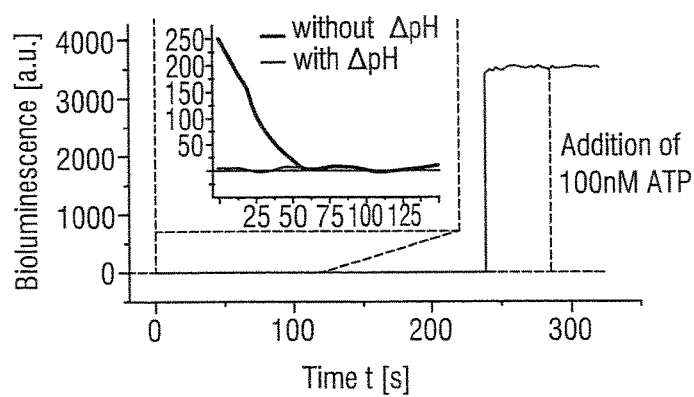

FIG. 12 shows a schematic illustration of $F_0F_1$-ATP synthase-reconstituted polymer shell-stabilized unilamellar vesicles as obtained in example 9 and of the transmembrane pH gradient—the driving force of ATP synthesis—as achieved by the addition of acidic FC-40 oil.

FIG. 13 shows the fluorescence intensity of the lipids at the droplets interface as a function of encapsulated lipid concentration of the experiments made in example 12.

FIG. 14 shows the stability of the lipid bilayer after release as performed in example 13. (A) oil phase (ATTO 520, yellow), (B) lipid bilayer (RhB DOPE, green), (C) encapsulated (HyLite 405, blue) and (D) continuous water phase (Alexa 647, red) were labeled with distinctive fluorophores. (E) A composite image of all channels.

Figure 15:
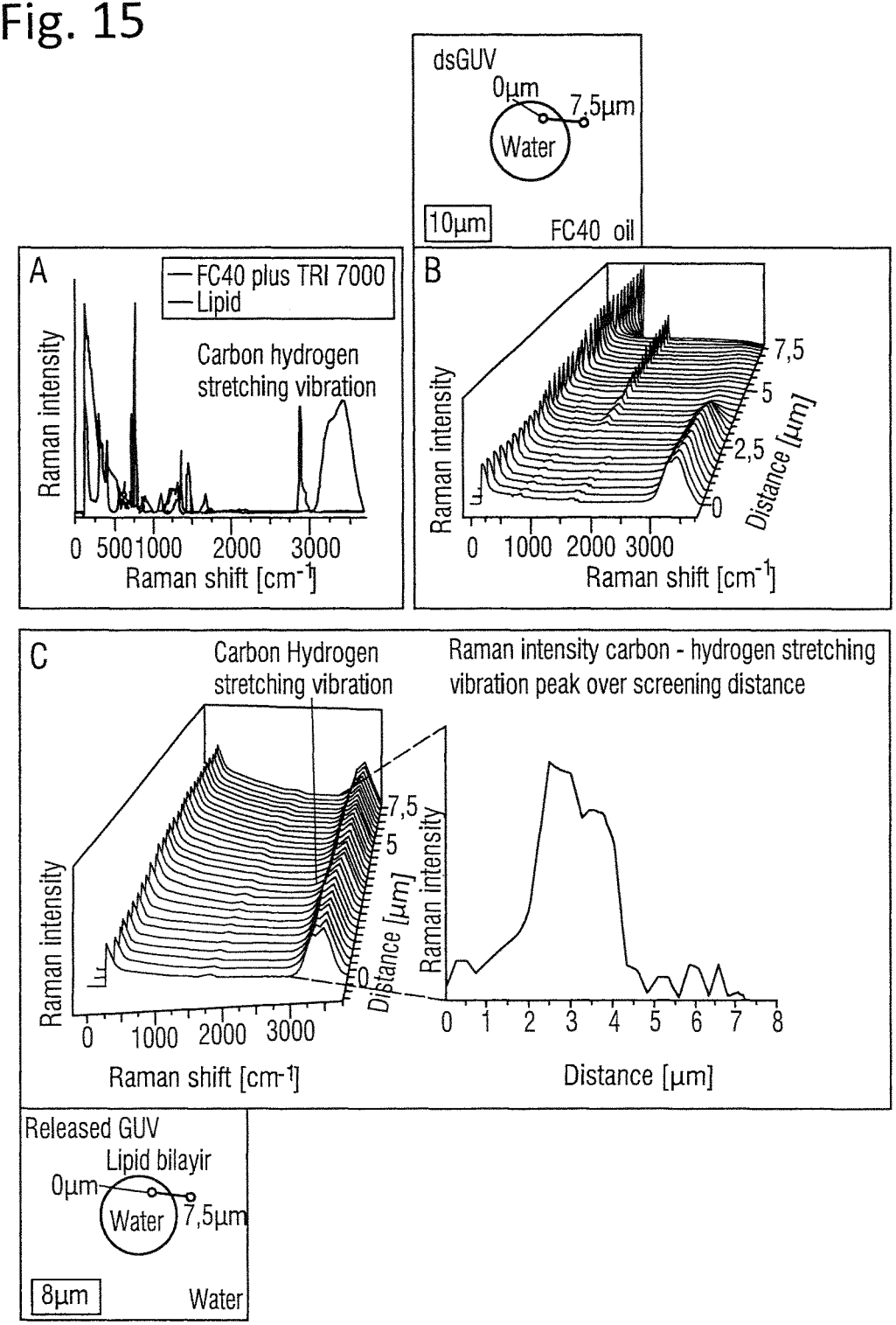

FIG. 15 Raman spectra of droplet-stabilized giant unilamellar vesicles and of respective released giant unilamellar vesicles without polymer shell as performed in example 14.

Figure 1:
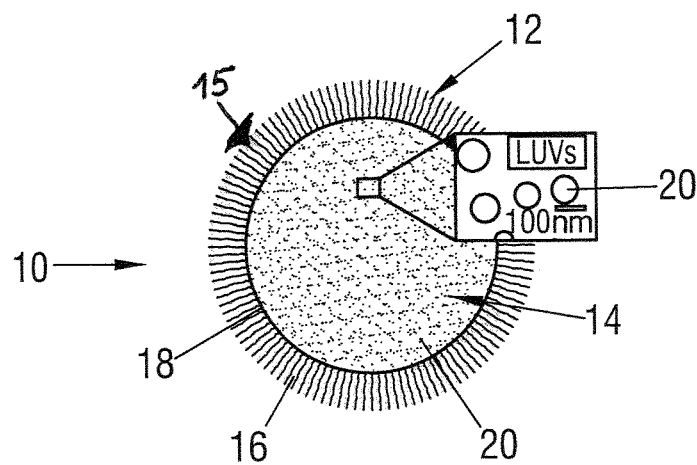
FIG. 1 shows a cross-section of a droplet encapsulated by an outer polymer shell, which borders the inner space of the droplet, wherein the droplet has a maximum dimension of 0.5 µm to 1,000 µm, wherein the inner space of the droplet contains at least one lipid, as obtained in step a) of the method in accordance with a preferred embodiment of the present invention.
Figure 3:
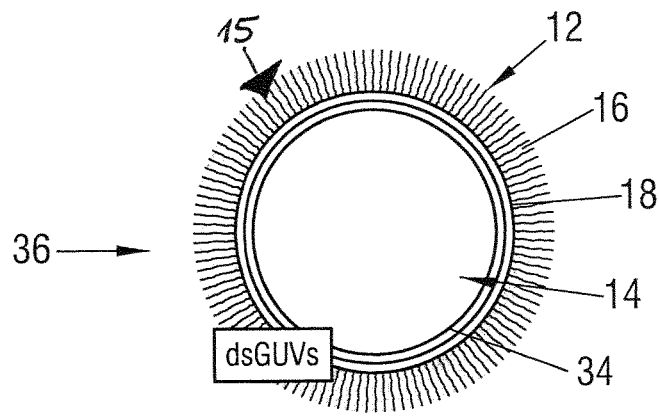
FIG. 3 shows a cross-section of a polymer shell-stabilized giant unilamellar vesicle with a lipid bilayer which is arranged at and covers the inner surface of the polymer shell, as obtained in step b) of the method in accordance with a preferred embodiment of the present invention.
Figure 4:
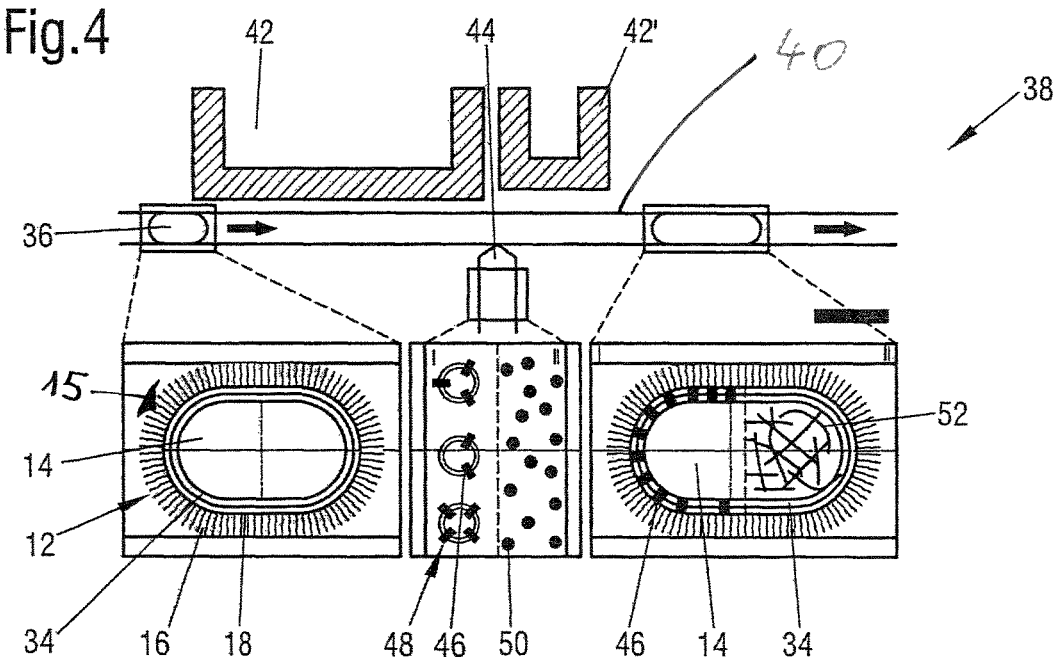
FIG. 4 shows a part of a pico-injector device for incorporating one or more proteins into the polymer shell-stabilized giant unilamellar vesicle for performing step c) according to one preferred embodiment of the present invention.

The droplet 10 schematically shown in cross-section in FIG. 1 as it is obtained in step a) of the method in accordance with the present invention is encapsulated by an outer polymer shell 12, which borders the inner space 14 of the droplet 10. The droplet 10 is spherical and has a diameter of 40 μm. The polymer shell 12 is made of an amphiphilic copolymer comprising a hydrophobic perfluorinated polyether block 16 arranged at the outer side and a hydrophilic polyether glycol block 18 arranged at the inner side of the polymer shell 12. For schematic reasons, the hydrophilic polyether glycol block 18 is shown in FIGS. 1, 3 and 4 as black ring. In the inner space 14 of the droplet 10, lipid in form of large or small unilamellar lipid-vesicles 20 having a diameter of about 80 nm are included. These large and small unilamellar lipid-vesicles 20 may be formed for example by dissolving the lipids in a solvent, such as chloroform, drying the so obtained mixture under inert gas atmosphere, resuspending the dried lipid in a buffer, vortexing the mixture and homogenizing the vesicle size by extruding the so obtained mixture through a filter.

Figure 2:
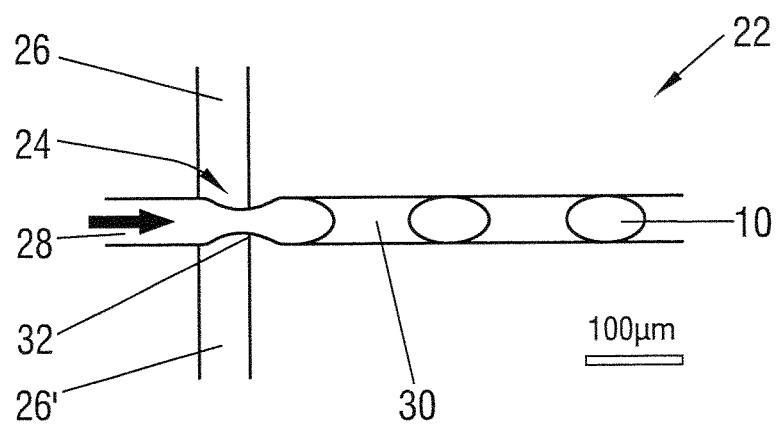
FIG. 2 shows the nozzle design of a flow-focusing microfluidic device for the generation of a droplet encapsulated by an outer polymer shell, which borders the inner space of the droplet, in which at least one lipid is included, which may be used for performing step a) and/or step b) according to one preferred embodiment of the present invention.

In a preferred embodiment of the present invention, the lipid 20 containing droplet 10 with outer polymer shell 12 as shown in FIG. 1 is prepared by droplet generation in a flow-focusing microfluidic device. This technique may be conducted in accordance with an embodiment of the present invention in a flow-focusing microfluidic device 22 having a nozzle design as shown in FIG. 2. More specifically, the flow-focusing microfluidic device 22 may comprise a junction 24, which is formed of three inlet channels 26, 26', 28 converging into a main channel or outlet channel 30, respectively, via a narrow orifice 32. Two of three inlet channels 26, 26' are arranged in the vertical direction, wherein both vertical inlet channels 26, 26' converge at the flow-focusing junction 24, one inlet channel 26 coming from above and one inlet channel 26' coming from below the flow-focusing junction 24. Furthermore, the third inlet channel 28 is arranged in the horizontal direction and meets the other two inlet channels 26, 26' at the flow-focusing junction 24 coming from the left side. The main channel or outlet channel 30, respectively, is also arranged in the horizontal direction and starts with its narrow orifice 32 on the side opposite the terminal end of the horizontal inlet channel 28. During the operation, the continuous oil phase comprising the amphiphilic copolymer(s) (which later form the polymer shell) dispersed or dissolved in oil, flows through the two vertical inlet channels 26, 26', wherein both continuous oil phase partial streams converge at the flow-focusing junction 24. The dispersed aqueous phase including the lipid(s) flows through the horizontal inlet channel 28 and is squeezed at the flow-focusing junction 24 by the oil-phase flowing through the two vertical inlet channels 26, 26'. Both phases pass through the small orifice 32 that is located downstream the three inlet channels 26, 26', 28, wherein the stream of the dispersed phase becomes narrow and breaks into droplets 10 of the lipid containing aqueous phase, wherein the droplets 10 are covered by the amphiphilic copolymer(s) thus forming a polymer shell, with the lipophilic or hydrophobic end of the copolymer being oriented at the outer shell side 15 towards the continuous oil phase and the hydrophilic end of the copolymer being oriented at the inner shell side towards the dispersed, lipid containing aqueous phase. The droplet size can be adjusted by the flow rates of the two phases, by the flow rate ratio and by the channel geometries.

In method step b), the lipid content 20 of the droplet 10 is transformed into a lipid bilayer which is arranged at and covers the inner surface of the polymer shell 12 in order to form a polymer shell-stabilized giant unilamellar vesicle. As described above, this may be achieved by adjusting the magnesium ion concentration of the lipid 20 containing aqueous phase included in the inner space 14 of the droplet 10 to 10 mM, wherein the concentration of magnesium ions within the inner space 14 of the droplet 10 may be adjusted during the droplet 10 formation described above in connection with FIG. 2. In this case, an aqueous, lipid 20 containing phase with a magnesium ion concentration of 10 mM is used in the third inlet channel 28 when operating the flow-focusing microfluidic device 22 shown in FIG. 2 and as described above. Thereby, the large and small unilamellar lipid-vesicles 20 in droplet 10 transform to a lipid bilayer 34, which is arranged at and covers the inner surface of the polymer shell 12 in order to form a polymer shell-stabilized giant unilamellar vesicle 36 as it is shown in FIG. 3.

The polymer shell-stabilized giant unilamellar vesicle 36 is chemically and mechanically notably stable so that it can be easily treated with a pico-injection technology, and thus can be easily loaded with proteins, such as transmembrane proteins and cytoskeleton proteins, as it is schematically shown in FIG. 4. The pico-injector device 38 comprises a channel 40, in which a dispersion of polymer shell-stabilized giant unilamellar vesicles 36 is flown. On one side of the channel 40 two electrodes 42, 42' are arranged, which apply an alternating electrical potential on the channel 40, whereas on the other side of the channel 40 a pico-injector 44 is arranged, through which liquid may be injected into the channel. During operation, an alternating electric potential, such as of 250 V and 1 kHz, is applied, which reduces the stability of the polymer shell 12, whereby the incorporation of the lipid and/or protein containing aqueous liquid provided by the pico-injector 44 into the polymer shell-stabilized giant unilamellar vesicle is enabled. Thereby, proteins may be incorporated into the lipid bilayer 34 and/or into the inner space 14 of the polymer shell-stabilized giant unilamellar vesicles 36. In particular, transmembrane proteins 46 may be injected and incorporated into the lipid bilayer 34 of the polymer shell-stabilized giant unilamellar vesicles 36. In this case, the transmembrane protein(s) 46 is injected into the polymer shell-stabilized giant unilamellar vesicles 36 preferably in form of proteoliposomes 48, which are liposomes, i.e. vesicles having at least one lipid bilayer, into which the one or more transmembrane proteins 46 have been inserted. Alternatively or in addition thereto, one or more cytoskeleton proteins 50 may be incorporated into the inner space 14 of the polymer shell-stabilized giant unilamellar vesicles 36, which may later form filaments 52.

Figure 5:
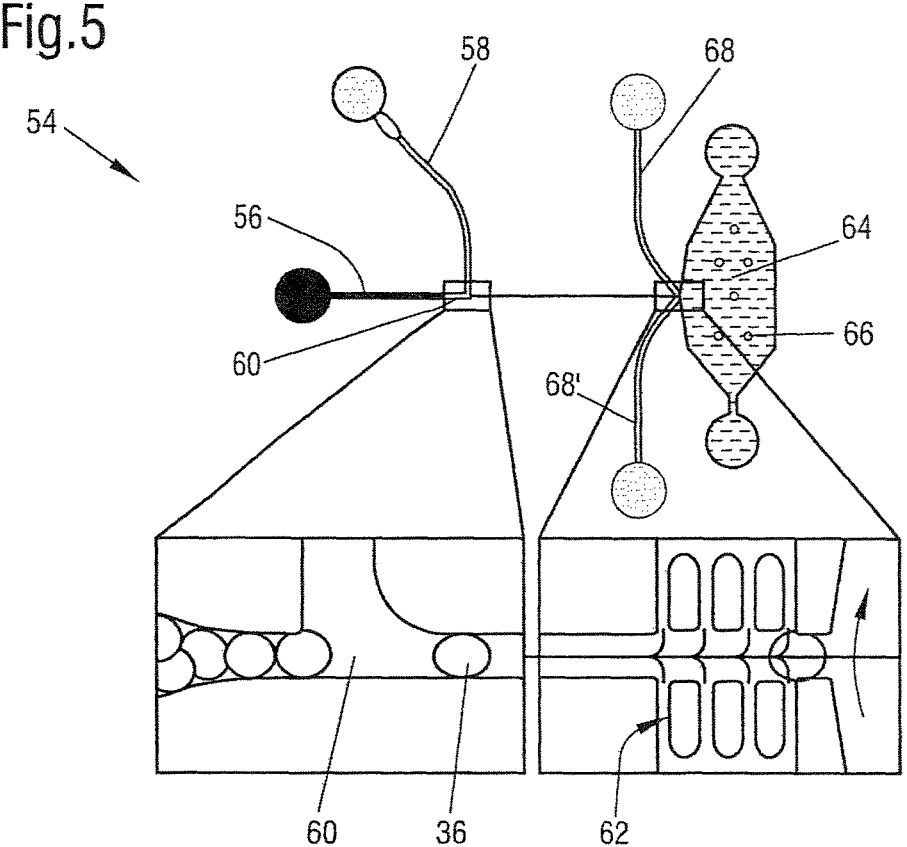
FIG. 5 shows schematically a microfluidic device for removing the polymer shell from the polymer shell-stabilized giant unilamellar vesicle for performing step d) according to one preferred embodiment of the present invention.

After incorporating the protein(s) into the polymer shell-stabilized giant unilamellar vesicle 36, the polymer shell 12 is not necessary any more. Therefore, it is preferred in accordance with the present invention to remove the polymer shell 12 and the oil phase 15 afterwards in step d) and preferably by a microfluidics technique. As shown in FIG. 5, the microfluidics device 54 may comprise a first inlet channel 56 for introducing the polymer shell-stabilized giant unilamellar vesicle 36 and a second inlet channel 58 for introducing a dispersion of polymer shell destabilizing surfactant(s) in oil into the first inlet channel 56. For this purpose, the first and second inlet channels 56, 58 are connected via a T-junction 60. Furthermore, downstream the T-junction 60, passive trapping structures 62 are provided, which decelerate the polymer shell-stabilized giant unilamellar vesicle 36. Further downstream, i.e. downstream the passive trapping structures 62, the first inlet channel 56 merges into a wide perpendicular channel 64, in which aqueous phase is flowing. Preferably, the total flow is adjusted in the microfluidic device during the operation so as to give the destabilizing surfactant(s) introduced via the second inlet channel 58 sufficient time to destabilize the polymer shell 12 of the polymer shell-stabilized giant unilamellar vesicle 36 in the first inlet channel 56. In addition, the height of the first inlet channel 56 is preferably designed to exceed the diameter of the polymer shell-stabilized giant unilamellar vesicle 36 and the pressure in the first inlet channel 56 is preferably adjusted to a maximum of 20 mbar, so as to minimize shear forces within the first inlet channel 56. As destabilizing surfactant, for instance an oil flow containing 20% by volume perfluoro-1-octanol may be used. Upon contact of the polymer shell-stabilized giant unilamellar vesicle 36 with the aqueous phase at the junction of the first inlet channel 56 and the wide perpendicular channel 64, in which the aqueous phase is flowing, the giant unilamellar vesicle 66 without polymer shell is released into the aqueous phase. In order to avoid that oil penetrates into the aqueous channel 64 whenever there are any droplets in the trapping structures, the aqueous flow is adjusted to achieve a zero-pressure gradient at the oil/water junction. As a result, the oil flows into the adjacent oil outlet channels 68, 68'.

Figure 6:
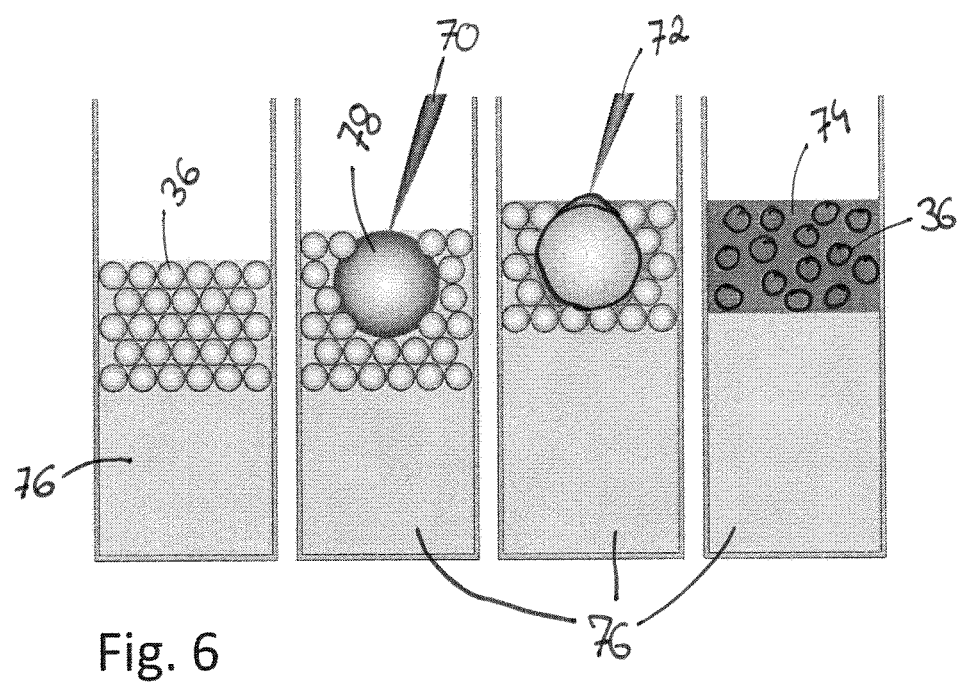
FIG. 6 shows schematically a bulk technique for removing the polymer shell and the oil phase from the polymer shell-stabilized giant unilamellar vesicle for performing step d) according to one preferred embodiment of the present invention.

In accordance with optional step d), the polymer shell 12 and the oil phase 15 are removed from the polymer shell-stabilized giant unilamellar vesicle 36 as shown in FIG. 6. Since the polymer shell 12 is not necessary any more after the incorporation of the one or more proteins into the polymer shell-stabilized giant unilamellar vesicle 36, which requires the mechanical stability effected by the polymer shell 12, it is actually preferred to perform the step d) so as to obtain a giant unilamellar vesicle 36. In addition, it is required to disperse the giant unilamellar vesicle 36 after removal of the polymer shell 12 and the oil phase 15 in an aqueous phase.

The removal step may also be performed by means of a bulk technique shown in FIG. 6. 100 μl of formed polymer shell-stabilized giant unilamellar vesicles 36 is collected in an Eppendorf tube for the bulk removal approach. Due to the density differences between the fluorinated oil 76 and water, the polymer shell-stabilized giant unilamellar vesicles 36 form a dense layer at the top of the tube. To provide an aqueous phase for polymer shell removal, 100 μl of buffer 70 is added as one large drop 78 in the center of the polymer shell-stabilized giant unilamellar vesicles 36 layer. To reduce the osmotic pressure effect, it is preferable if the buffer ionic content will be identical to the buffer content within the polymer shell-stabilized giant unilamellar vesicles 36. Following the addition of buffer, an oil 72 containing 20% by volume of perfluoro-1-octanol is dripped on top of the buffer drop 78. After applying the complete volume of destabilizer, the tube is tilted to increase the interface area and slowly rotated about its longitudinal axis. In these conditions the emulsion breakage takes less than five minutes. The aqueous solution 74 containing giant unilamellar vesicles 36 without polymer shell 12 can be carefully removed with a pipette.

Subsequently, the present invention is described by means of examples, which do, however, not limit the present patent application.

EXAMPLE 1

(Production of Polymer Shell-Stabilized Giant Unilamellar Vesicle)
Synthesis of Amphiphilic Block Copolymer for the Polymer Shell A block-copolymer surfactant was synthesized according to protocols reported by Platzman, I., Janiesch, J.-W. & Spatz, J. P. Synthesis of Nanostructured and Biofunctionalized Water-in-Oil Droplets as Tools for Homing T Cells. J. Am. Chem. Soc. 135, 3339-3342 (2013) and by Janiesch, J. W. et al. Key factors for stable retention of fluorophores and labeled biomolecules in droplet-based microfluidics. Anal Chem 87, 2063-2067 (2015). More specifically, a triblock copolymer perfluoro polyether (PFPE) (7,000 g/mol)-polyethylene glycol (PEG) (1,400 g/mol)-PFPE(7000 g/mol) (TRI7000) and a gold-linked diblock-copolymer surfactant Au-PEG (436 g/mol)-PFPE (7000 g/mol) were synthesized. After the synthesis, the triblock surfactant was mixed separately with the gold-linked surfactant and dissolved in FC-40 fluorinated oil (3M, USA) to the final concentrations of 2.5 mM and 3 µM for triblock and gold-linked surfactants, respectively.

IR measurements were performed to confirm the success of the copolymer synthesis and to evaluate the purity. FC-40 perflourinated oil was used as a background solvent to obtain the spectra. The measurements were conducted on a Nicolet Nexus 870 Fourier transform infrared spectrophotometer (Thermo Electron GmbH, Dreieich, Germany) using a demountable pathlength cell for liquid FTIR (Thermo Scientific, USA) with KBr glasses and FC-40 perflourinated oil as solvent.

FIG. 7 (A) shows the representative FTIR spectra of the PFPE(7000)-carboxylic acid reactant and the triblock surfactant product PFPE(7000)-PEG(1400)-PFPE(7000) (TRI7000). This figure presents five major bands at 1701, 1775, 2848, 2956 and 3556 $cm^{-1}$. The band at 1701 $cm^{-1}$ is attributed to the ester (C=O) stretching mode. The band at 1775 $cm^{-1}$ is attributed to a stretching mode of the (C=O) bond of the PFPE-carboxylic acid which is strongly blue-shifted (by ~50 $cm^{-1}$) due to the electronegative fluor atoms in alpha position to the carboxylic group. The same blueshift of the carboxylic (C=O) band was observed previously in the studies measuring the FTIR spectrum of the trifluoroacetic acid. The bands at 2848 and 2956 $cm^{-1}$ are assigned to symmetric and asymmetric stretching modes of the PEG (C—H) groups of the PFPE-PEG-PFPE product. The band at 3556 $cm^{-1}$ is assigned to the asymmetric stretching (OH) vibrations.

FIG. 7 (B) shows representative FTIR spectra of the DI7000 and PFPE(7000)carboxylic acid. This figure presents major bands at 1698, 1775, 2889, 2993 and 3556 $cm^{-1}$. The band at 1698 $cm^{-1}$ represents a stretching mode of the ester v(C=O). The broad band at 2889 and 2993 $cm^{-1}$ represents the symmetric and asymmetric stretching of PEG $v_a(CH)$. The band at 3556 $cm^{-1}$ is assigned to the asymmetric stretching (OH) vibrations.

Electroformation

Lipid in form of giant unilamellar vesicles consisting of 1,2-dioleoyl-sn-glycero-3-phosphocholine (DOPC):1,2-dioleoyl-sn-glycero-3-phosphoethanolamine (DOPE): 1,2-dioleoyl-sn-glycero-3-phospho-L-serine (DOPS) in a weight ratio 8:1:1 further including 1% ATTO 488-labeled DOPE were formed using the electroformation protocols as described by Herold, C., Chwastek, G., Schwille, P. & Petrov, E. P. Efficient Electroformation of Supergiant Unilamellar Vesicles Containing Cationic Lipids on ITO-Coated Electrodes. Langmuir 28, 5518-5521 (2012). More specifically, the lipid mixture at a concentration of 5 mM was dissolved in pure chloroform and spread onto two indium tin oxide (ITO) coated glasses (Sigma-Aldrich, Germany). Following chloroform evaporation, the electroformation cell was assembled. Towards this end, the two ITO coated glasses were faced to each other with the conductive sides. To avoid direct contact two Teflon spacers (1 mm) were used. Copper tape (3M, USA) was used to connect the conducting sides with a signal generator (RS Components, Germany). Subsequently, the chamber was filled with Milli-Q water (Millipore filtered) having a magnesium ion concentration of 10 mM and sealed with two-component glue (Twinsil Picodent GmbH, Germany). An alternating electrical potential of 10 Hz at 1 V amplitude was applied for 2 h to form the giant unilamellar vesicles. Following vesicles production, the solutions were used immediately for encapsulation into microfluidic water-in-oil copolymer-stabilized droplets.

Formation of a Polymer Shell, in which the Lipids are Included, by Microfluidics and Transformation of the Lipids into a Lipid Bilayer:

A droplet-based microfluidic device made of polydimethylsiloxane (PDMS) (Sylgard 184, Dow Corning, USA) was prepared by photo- and soft-lithography methods as described by Gu, H., Duits, M. H. G. and Mugele, F. Droplets Formation and Merging in Two-Phase Flow Microfluidics. International Journal of Molecular Sciences 12, 2572-2597 (2011) and by Xia, Y. & Whitesides, G. M. SOFT LITHOGRAPHY. Annual Review of Materials Science 28, 153-184 (1998). To control the droplet diameter during their creation, the nozzle designs at the flow-focusing junction was implemented as shown in FIG. 2. Syringe pumps PUMP 11 ELITE (Harvard apparatus, USA) were used to control flow rates of 120 µL/h for the aqueous phase and 160 µL/h for the oil phase as required for stable droplet creation (diameter d=40 µm) at the rate of 1 kHz. The oil phase included the amphiphilic block copolymer synthesized as described above and the aqueous phase included the lipids synthesized as described above and had a magnesium ion concentration of 10 mM as described above. On account of the magnesium ion concentration adjusted to be 10 mM in the aqueous phase, the lipid mixture included in the inner space of the droplet transformed into a lipid bilayer being arranged at the inner surface of the polymer shell. Thus, polymer shell-stabilized giant unilamellar vesicles were formed.

The schematic structure of the so obtained polymer shell-stabilized giant unilamellar vesicle is shown in FIG. 3.

EXAMPLE 2

(Formation and Release of Different Giant Unilamellar Vesicles from Polymer Shell-Stabilized Giant Unilamellar Vesicles)

In general, the determined concentration (minimal 950 µM for polymer shell-stabilized giant unilamellar vesicles with 30 µm in diameter, usually 1 to 2 mM was used) of lipids in form of small unilamellar vesicles dissolved in Milli-Q water was encapsulated into polymer shell-stabilized giant unilamellar vesicles of 30 µm in diameter as produced according to example 1 and as shown in FIG. 1. Different lipid composition could be used to generate neutrally, negatively or positively charged giant unilamellar vesicles in polymer stabilized droplets and its release.

To transform the encapsulated small unilamellar vesicles in the case of neutral and negatively charged polymer shell-stabilized giant unilamellar vesicles into a continuous supported lipid bilayer at the droplet inner interface, a solution with the optimized $MgCl_2$ concentration of 10 mM was introduced during droplet production or by means of pico-injection in a device as shown in FIG. 4. The lipid bilayer was formed within seconds. $Mg^{2+}$ ions are considered to be the most efficient mediators of lipid vesicle rupture, because they promote adhesion to a supporting surface.

To transform the encapsulated small unilamellar vesicles in the case of positively charged polymer shell-stabilized giant unilamellar vesicles into a continuous supported lipid bilayer at the droplet inner interface, small unilamellar vesicles containing at least 20 mol % positively charged lipids (and a clear excess of positively charged lipids towards negatively charged lipids) do not need any addition of ions to create polymer shell-stabilized giant unilamellar vesicles. Positively charged polymer shell-stabilized giant unilamellar vesicles are forming also without additions of ions due to direct electrostatic interactions with the negatively charged inner surface of the polymer shell (PFPE-PEG) pointing into the aqueous phase. Therefore, the positively charged small unilamellar vesicles adhere and immediately rapture to form a lipid bilayer at the inner surface of the polymer shell. Giant unilamellar vesicles release was successfully tested for a concentration of up to 40 mol % positively charged lipids.

Release of Giant Unilamellar Vesicles from Polymer Shell-Stabilized Giant Unilamellar Vesicles
Bulk Release Technique:

For the successful release of giant unilamellar vesicles, the lipid compositions of the polymer shell-stabilized giant unilamellar vesicles were optimized for each case as shown in the subsequent Tables 1 and 2. The following method for the release of giant unilamellar vesicles out of the oil phase into the aqueous phase was used for every type of polymer shell-stabilized giant unilamellar vesicles described before.

Following the formation of polymer shell-stabilized giant unilamellar vesicles, 100 μL oil/polymer shell-stabilized giant unilamellar vesicle-containing solution was transferred into a 2 ml Eppendorf tube containing 1 ml FC-40 oil/surfactant solution (identical to the FC-40 oil/surfactant solution used for polymer shell-stabilized giant unilamellar vesicles). Next, 100 μl of the appropriate solution or buffer was pipetted on to the droplet emulsion. Usually the same buffer or solution as encapsulated by the polymer shell-stabilized giant unilamellar vesicles was used (e.g. MilliQ water, 10 mM $MgCl_2$, actin polymerization buffer, or integrin activation buffer). In order to destabilize the polymer shell of the droplets, 100 μl of 20 vol % perfluoro-1-octanol destabilizing surfactants (Sigma-Aldrich, Germany) dissolved in FC-40 oil were added. The Eppendorf tube was carefully tilted and slowly rotated until the emulsion was broken. The released giant unilamellar vesicles were studied in an observation chamber made of BSA-coated glass slides and cover slips. The observation chambers were prepared by incubating the glass with 10 mg/ml BSA in PBS for 2 h at room temperature, followed by two 5 min washing steps, one with PBS and one with water.

TABLE 1

| Release of positively charged giant unilamellar vesicles | |
|---|---|
| 40 mol % DOTAP<br>59.5 mol % DOPC<br>0.5 mol % RhB-DOPE<br>1.5 mM lipids in Milli-Q water | See FIG. 8.1 |
| 40 mol % DOTAP<br>20 mol % cholesterol<br>39.5 mol % DOPC<br>0.5 mol % RhB-DOPE<br>1.5 mM lipids in Milli-Q water | See FIG. 8.2 |
| 40 mol % DOTAP<br>10 mol % DOPG<br>49.5 mol % DOPC<br>0.5 mol % Atto488-DOPE<br>1.5 mM lipids in Milli-Q water | See FIG. 8.3 |
| 20 mol % DOTAP<br>10 mol % cholesterol<br>69.5 mol % DOPC<br>0.5 mol % Atto488-DOPE<br>2 mM lipids in Milli-Q water | See FIG. 8.4 |
| 20 mol % DOTAP<br>10 mol % cholesterol<br>69.5 mol % DOPC<br>0.5 mol % Atto488-DOPE<br>2 mM lipids in 20 mM MgCl2 | See FIG. 8.5 |
| 30 mol % DOTAP<br>10 mol % cholesterol<br>59.5 mol % DOPC<br>0.5 mol % Atto488-DOPE<br>2 mM lipids in Milli-Q water | See FIG. 8.6 |
| 40 mol % DOTAP<br>10 mol % cholesterol<br>49.5 mol % DOPC<br>0.5 mol % Atto488-DOPE<br>2 mM lipids in Milli-Q water | See FIG. 8.7 |
| 20 mol % DOTAP<br>20 mol % cholesterol<br>59.5 mol % DOPC<br>0.5 mol % Atto488-DOPE<br>2 mM lipids in Milli-Q water | See FIG. 8.8 |
| 20 mol % DOTAP<br>20 mol % cholesterol<br>59.5 mol % DOPC<br>0.5 mol % Atto488-DOPE<br>2 mM lipids in 20 mM Tris-HCl pH 7.4, 50 mM NaCl, 1 mM $CaCl_2$ | See FIG. 8.9 |
| 30 mol % DOTAP<br>20 mol % cholesterol<br>49.5 mol % DOPC<br>0.5 mol % Atto488-DOPE<br>2 mM lipids in Milli-Q water | See FIG. 8.10 |
| 30 mol % DOTAP<br>10 mol % DOPG<br>10 mol % cholesterol<br>49.5 mol % DOPC<br>0.5 mol % Atto488-DOPE<br>2 mM lipids in Milli-Q water | See FIG. 8.11 |
| 40 mol % DOTAP<br>10 mol % DOPG<br>10 mol % cholesterol<br>39.5 mol % DOPC<br>0.5 mol % Atto488-DOPE<br>2 mM lipids in Milli-Q water | See FIG. 8.12 |
| 20 mol % DOTAP<br>20 mol % cholesterol<br>59.5 mol % POPC<br>0.5 mol % Atto488-DOPE<br>2 mM lipids in Milli-Q water | See FIG. 8.13 |
| 10 mol % DOTAP<br>20 mol % cholesterol<br>69.5 mol % DOPC<br>0.5 mol % Atto488-DOPE<br>2 mM lipids in 10 mM $MgCl_2$ | See FIG. 8.14 |

TABLE 2

| Release of neutral and negatively charged giant unilamellar vesicles | |
|---|---|
| 10 mol % DOPG<br>10 mol % cholesterol<br>79.5 mol % DOPC<br>0.5 mol % Atto488-DOPE<br>1.5 mM lipids in 10 mM MgCl2 | See FIG. 9.1 |
| 10 mol % DOPG<br>20 mol % cholesterol<br>69.5 mol % DOPC<br>0.5 mol % Atto488-DOPE<br>2 mM lipids in 10 mM MgCl$_2$ | See FIG. 9.2 |
| 79.5 mol % POPC<br>20 mol % cholesterol<br>0.5 mol % Atto488-DOPE<br>2 mM lipids in 10 mM MgCl$_2$ | See FIG. 9.3 |
| 40 mol % POPC<br>40 mol % DOPC<br>19.5 mol % cholesterol<br>0.5 mol % Atto488-DOPE<br>1.5 mM lipids in 20 mM TRIS/HCl,<br>pH 7.4, 50 mM NaCl, 1 mM CaCl$_2$,<br>10 mM MgCl$_2$ | See FIG. 9.4 |
| 40 mol % POPC<br>40 mol % DOPC<br>19.5 mol % cholesterol<br>0.5 mol % Atto488-DOPE<br>2 mM lipids in 10 mM MgCl$_2$ | See FIG. 9.5 |
| 40 mol % POPC<br>40 mol % DOPC<br>19.5 mol % cholesterol<br>0.5 mol % Atto488-DOPE<br>2 mM lipids in 20 mM MgCl$_2$ | See FIG. 9.6 |
| 36 mol % DOPC<br>36 mol % POPC<br>17.5 mol % cholesterol<br>10 mol % EggPC<br>1.5 mol % Atto488-DOPE<br>1.5 mM lipids in integrin<br>activation buffer (20 mM<br>TRIS/HCl, pH 7.4, 50 mM NaCl,<br>0.5 mM CaCl$_2$, 1 mM MnCl$_2$ and<br>1 mM MgCl$_2$) | See FIG. 9.7 |
| 36 mol % DOPC<br>36 mol % POPC<br>17.5 mol % cholesterol<br>10 mol % EggPC (with integrin)<br>0.5 mol % Atto488-DOPE<br>1.5 mM lipids in integrin activation buffer | See FIG. 9.8 |
| 36 mol % DOPC<br>36 mol % POPC<br>17.5 mol % cholesterol<br>5 mol % EggPC<br>5 mol % EggPG<br>0.5 mol % Atto488-DOPE<br>1.5 mM lipids in integrin activation buffer | See FIG. 9.9 |
| 36 mol % DOPC<br>36 mol % POPC<br>17.5 mol % cholesterol<br>5 mol % EggPC<br>5 mol % EggPG (with integrin)<br>0.5 mol % Atto488-DOPE<br>1.5 mM lipids in integrin activation buffer | See FIG. 9.10 |
| 32 mol % DOPC<br>32 mol % POPC<br>15.5 mol % cholesterol<br>20 mol % EggPC<br>0.5 mol % Atto488-DOPE<br>1.5 mM lipids in integrin activation buffer | See FIG. 9.11 |
| 32 mol % DOPC<br>32 mol % POPC<br>15.5 mol % cholesterol<br>20 mol % EggPG (with integrin)<br>0.5 mol % Atto488-DOPE<br>1.5 mM lipids in integrin activation buffer | See FIG. 9.12 |
| 5 mol % DOPG<br>20 mol % cholesterol<br>74.75 mol % DOPC<br>0.25 mol % Atto488-DOPE<br>2 mM lipids in actin polymerization buffer<br>(2.0 mM TRIS/HCl pH 8, 0.2<br>mM CaCl$_2$, 0.5 mM ATP, 0,005% NaN$_3$ and 0.2 mM<br>DTT) with 15 mM MgCl$_2$ | See FIG. 9.13 |
| 3 mol % DOPG<br>20 mol % cholesterol<br>76 mol % DOPC<br>1 mol % Atto488-DOPE (containing actin)<br>1.1 mM lipids in actin polymerization<br>buffer with 25 mM MgCl$_2$ | See FIG. 9.14 |

EXAMPLE 3

(Polymer Shell-Stabilized Giant Unilamellar Vesicles Containing Integrin Proteins—Method 1)

Integrin $\alpha_{IIb}\beta_3$ was reconstituted into large unilamellar vesicles by the detergent removal method. Therefore, dried egg PC was dissolved in a buffer containing 0.1% of Triton X-100. Integrin $\alpha_{IIb}\beta_3$ was added to a 1:1000 integrin-lipid ratio. The solution was incubated at 37° C. for 2 hours in a shaker at 600 rpm. Triton X-100 was removed in two subsequent washing steps of 3.5 hours using 50 mg/ml SM-2 Bio-beads. The size distribution of liposomes and integrin-liposomes was measured by dynamic light scattering in a Malvern Zetasizer Nano ZS setup (Malvern, UK) to be around 100 to 140 nm. Polymer shell-stabilized giant unilamellar vesicles containing integrin $\alpha_{IIb}\beta_3$ were formed as described in example 1 while encapsulating a lipid mixture containing 10% large unilamellar vesicles with reconstituted integrin $\alpha_{IIb}\beta_3$ during droplet formation.

EXAMPLE 4

(Polymer Shell-Stabilized Giant Unilamellar Vesicles Containing Integrin Proteins—Method 2)

Integrin $\alpha_{IIb}\beta_3$ was reconstituted into large unilamellar vesicles by the detergent removal method as described in example 3.

Simultaneously, polymer shell-stabilized giant unilamellar vesicles were formed and collected after production as described in example 1.

Following these preparatory steps, the droplets were injected into a pico-injection device as shown in FIG. 4. Therefore, a microfluidic flow control system (MFCS-EZ, Fluigent, France) was used to control the pressure on all inlet channels. The spacing of the droplets was controlled via a confluent oil channel.

Following the separation step, isolated droplets passed an electric AC field (frequency of 1 kHz, voltage of 250 V) generated by a HM 8150 signal generator (HAMEG, Germany) and amplified by a 623B—H—CE linear amplifier (TREK, USA) attached to two electrodes made of Indalloy 19 (51% indium, 32.5% bismuth, 16.5% tin, Indium Cooperation, USA). The solution containing the Integrin-LUV was connected to the injection channel. By exposing the droplet to an electric field with a potential of 250 V and 1 kHz the polymer shell is destabilized. This facilitates coalescence with a second aqueous phase at the nozzle of the adjacent injection channel. Through control of the pressure differential between the main and the adjacent channel the injection into the droplets can be finely regulated.

The injected Integrin-large unilamellar vesicles fused with the existing polymer shell-stabilized giant unilamellar vesicle.

EXAMPLE 5

(Polymer Shell-Stabilized Giant Unilamellar Vesicles Containing Integrin Proteins—Method 3)

Instead of reconstituting the integrin $\alpha_{IIb}\beta_3$ into LUV as stated in example 3, the protein was solubilized using 0.1% Triton X-100. All other steps from example 4 were kept consistent. Due to poration induced by the electric field of pico-injection into the polymer shell-stabilized giant unilamellar vesicle the integrin $\alpha_{IIb}\beta_3$ inserts into the lipid membrane.

EXAMPLE 6

(Polymer Shell-Stabilized Giant Unilamellar Vesicles Containing Integrin Proteins Interact with the Biofunctionalized Inner Polymer Shell of the Droplets)

Formation of polymer stabilized water droplets in an oil phase was done as described in example 1. By use of gold nanoparticle-linked block copolymers, the inner droplet interface was functionalized. For example, a ligand mimetic peptide was bound to the gold nanoparticles via thiol chemistry, therefore, providing binding sites for integrin $\alpha_{IIb}\beta_3$. Using this approach, polymer shell-stabilized giant unilamellar vesicles containing reconstituted integrin $\alpha_{IIb}\beta_3$, produced according to examples 3 to 5, were linked to the polymer shell.

FRAP measurements of transmembrane proteins reconstituted into polymer shell-stabilized giant unilamellar vesicles revealed diffusion coefficients of $0.70\pm0.1$ $\mu m^2/s$ for integrin. Moreover, to test the functionality of the reconstituted integrin, RGD peptides anchored to gold-linked surfactants were used to provide binding sites for integrin adhesion. In this case, the diffusion coefficient of integrin dropped to $0.13\pm0.03$ $\mu m^2/s$ consistent with the mobility of the copolymer surfactant layer that stabilizes the droplet.

Successful binding between the integrin and the RGD on the droplet interface indicated the functional incorporation of integrin into the lipid bilayer of the polymer shell-stabilized giant unilamellar vesicles. It also reveals that at least part of the integrin proteins are oriented correctly, with their extracellular parts pointing towards the inner interface of the copolymer shell that stabilizes droplet.

Functionalization of Gold-Linked Surfactant

To provide adhesion sites for integrin on the surface of gold-nanostructured droplets, a two-step protocol was devised to functionalize the GNPs with a RGD-mimetic-peptide via thiol chemistry.

Freeze-dried PFPE-PEG-Au diblock-copolymer surfactants were dissolved in 100 μl of fluorinated oil FC-40 at a concentration of 25 μM. An aqueous solution containing the RGD peptides (50 μM, 100 μl) was added and the emulsion was stirred for 1 hour. To remove unbound RGD peptides, the emulsion was centrifuged, which led to the sedimentation of the heavier oil. Subsequently, the supernatant was discarded and the precipitant was freeze-dried for 24 hours to remove any remaining water.

Finally, the product was dissolved in 1 ml of (the oil) FC-40 and filtered with a hydrophobic filter (PTFE 0.2 μm), removing traces of unreacted peptide.

EXAMPLE 7

(Release of Integrin-Functionalized Giant Unilamellar Vesicles and Integrin Functionality Assessment)

Formation of polymer stabilized water droplets in an oil phase was done as described in example 1.

Then, polymer shell-stabilized giant unilamellar vesicles containing reconstituted integrin $\alpha_{IIb}\beta_3$ were produced according to examples 3 to 5 and collected in a reaction tube.

Release of integrin-functionalized giant unilamellar vesicles was done by bulk release technique as described in example 2. The aqueous solution containing released giant unilamellar vesicles was carefully removed by pipetting and immediately used for observation or experiments.

The released giant unilamellar vesicles showed an even distribution of fluorescently labeled integrin as shown in FIG. 10. To validate the functionality of the reconstituted integrin $\alpha_{IIb}\beta_3$, the spreading behavior of the released integrin-functionalized giant unilamellar vesicles was investigated as shown in FIG. 10. While these integrin $\alpha_{IIb}\beta_3$-protocells do not spread on BSA-coated interfaces, they spread well on fibrinogen but less on fibronectin or collagen matrices as it is expected from the platelet adhesion receptor integrin $\alpha_{IIb}\beta_3$. The differential adhesion on the various matrices further demonstrates that the protein reconstitution and release process does not affect the biological functionality of the integrin-functionalized giant unilamellar vesicles.

EXAMPLE 8

(Actin and Intergin Reconstitution within Polymer Shell-Stabilized Giant Unilamellar Vesicles)

Formation of polymer shell-stabilized water droplets in an oil phase was done as described in example 1. For the production of polymer shell-stabilized giant unilamellar vesicles containing both actin filaments and integrin $\alpha_{IIb}\beta_3$, integrin $\alpha_{IIb}\beta_3$ (50% TAMRA-labeled integrin $\alpha_{IIb}\beta_3$) was first reconstituted into large unilamellar vesicles consisting of 50% egg PC and 50% eggPG by detergent removal as described in example 1. These proteoliposomes were then mixed at a ratio of 1:9 with liposomes containing 76% DOPC, 20% cholesterol, 3% DOPG and 1% ATTO 488-labeled DOPE in 20 mM TRIS/HCl, pH 7.4, 50 mM NaCl, 0.5 mM $CaCl_2$, 25 mM $MgCl_2$ and subsequently used for polymer shell-stabilized giant unilamellar vesicle formation. As a second step, G-actin (1% Alexa Fluor 647-labeled actin, in 2.0 mM TRIS/HCl pH 8, 0.2 mM $CaCl_2$, 0.2 mM ATP, 0.005% $NaN_3$ and 0.2 mM DTT) was pico-injected into these droplets. Further the droplets were collected and transferred into an observation chamber to control the reconstitution of integrin within in the lipid bilayer and actin filaments within the polymer shell-stabilized giant unilamellar vesicles.

It was shown that that following all steps as presented in Example 8, actin filament and integrin proteins were successfully included in the polymer shell stabilized giant unilamellar vesicles as shown in FIG. 11.

FIG. 11 shows representative fluorescence images of the polymer shell-stabilized giant unilamellar vesicles (1% ATTO 488-labeled DOPE, first panel), the reconstituted TAMRA-labelled αIIbβ3 integrin (second panel), the actin cytoskeleton (1% Alexa Fluor 647-labeled actin, third panel) and the composite fluorescence image of all channels (titled merged—fourth panel) showing the actin and integrin reconstituted polymer shell-stabilized giant unilamellar vesicles 20.

EXAMPLE 9

(Incorporation of ATP-Synthase into the Lipid Bilayer)

Giant unilamellar vesicle formation within polymer droplets were prepared as described in example 1. $F_0F_1$-ATP synthase was isolated from *E. coli* and labeled with Alexa 488 as described by Zimmermann, B., Diez, M., Zarrabi, N., Graber, P. & Borsch, M: Movements of the epsilon-subunit during catalysis and activation in single membrane-bound H+-ATP synthase. Embo Journal 24, 2053-2063 (2005). Subsequently ATP-synthase was reconstituted into pre-formed liposomes (diameter d~120 nm diameter) in tricine buffer, consisting of 20 mM tricine-NaOH (pH 8.0), 20 mM succinic acid, 0.6 mM KCl, 50 mM NaCl and 2.5 mM $MgCl_2$ as described by Fischer and Graber: Comparison of Delta pH- and Delta phi-driven ATP synthesis catalyzed by the H+-ATPases from *Escherichia coli* or chloroplasts reconstituted into liposomes, Febs Letters 457, 327-332 (1999). Polymer shell-stabilized giant unilamellar vesicles were formed as described above using a lipid mixture of DOPC:DOPE:DOPS (8:1:1), including 1% Rhodamine B (RhB)-labeled DOPE in $F_0F_1$-ATP activity buffer, consisting of 20 mM tricine-NaOH (pH 7.5), 20 mM succinic acid, 10 mM $MgCl_2$, 5 mM $NaH_2PO_4$ and 50 µM ultra-pure ADP (Cell Technology, USA). Using the microfluidic pico-injector, the above-mentioned liposomes containing ATP-synthase were injected into the polymer shell-stabilized giant unilamellar vesicles as schematically shown in FIG. 4. The alternating electric potential of the electrodes of the pico-injector was set to 250 V and 1 kHz, whereat the pressure of the injection channel was adjusted in a way to inject around 10% of the droplets' volume. A successful fusion of the liposomes with the polymer shell-stabilized giant unilamellar vesicles was achieved as indicated by the colocalization of the Alexa 488 fluorescent ATP-synthase signal and the Rhodamine B fluorescent lipid signal.

For the activity assessment of the reconstituted $F_0F_1$-ATP synthase in polymer shell-stabilized giant unilamellar vesicles, the $F_0F_1$-ATP synthase has to be energized by a transmembrane pH gradient established between the $F_0F_1$-ATP synthase-containing polymer shell-stabilized giant unilamellar vesicles and the surrounding oil. To generate a pH gradient ($\Delta pH \approx 3$), 1 µL of trifluoroacetic acid (TFA, 99%, Sigma-Aldrich, Germany) was dissolved in 1 ml FC40 oil and an oil exchange was performed. Following the application of the acidic oil, the change in the droplets internal pH through proton diffusion was analyzed by pyranine intensity detection.

Following the reconstitution of the $F_0F_1$-ATP synthases in polymer shell-stabilized giant unilamellar vesicles, 100 µL oil/polymer shell-stabilized giant unilamellar vesicles solution was transferred to a 500 µL Eppendorf and 20 µL of acidic FC-40 oil was added by pipetting. The Eppendorf was carefully tilted and slowly rotated for 2 minutes. Then, 5 µL of perfluoro-1-octanol 20 vol % destabilizing surfactants (Sigma-Aldrich) was added to release the content of the droplets. To analyze the ATP content, 5 µL of the released aqueous solution was transferred to a well on a non-transparent 96 well plate with a flat bottom, containing 180 µL tricine buffer and 20 µL of 10-fold concentrated luciferase reagent (ATP Bioluminescence Kit CLS II, Sigma-Aldrich, Germany). A plate reader (Infinite M200, Tecan Switzerland) was used to detect the bioluminescence intensity corresponding to the synthesized ATP in the aqueous solution. As a control, the same amount of aqueous solution was released from the $F_0F_1$-ATP synthase-containing giant unilamellar vesicles that were not energized by a transmembrane pH gradient and analyzed.

To assess the amount of synthesized ATP, a bioluminescence calibration curve was produced by addition of 100 nM ATP solution as shown in FIG. 12. and of the transmembrane pH gradient—the driving force of ATP synthesis—as achieved by the addition of acidic FC-40 oil. The graph on the right shows the bioluminescence intensity response to the ATP content as a function of time. The inserted smaller graph shows the representative bioluminescence intensity curves obtained from the aqueous content of giant unilamellar vesicles activated (red) by a pH gradient and giant unilamellar vesicles without a pH gradient (black). The bioluminescence curve was calibrated by the addition of 100 nM ATP solution to assess the amount of synthesized ATP as shown in FIG. 12.

FIG. 12 shows a schematic illustration of $F_0F_1$-ATP synthase-reconstituted polymer shell-stabilized giant unilamellar vesicles and of the transmembrane pH gradient—the driving force of ATP synthesis—as achieved by the addition of acidic FC-40 oil. The graph on the right shows the bioluminescence intensity response to the ATP content as a function of time. The inserted smaller graph shows the representative bioluminescence intensity curves obtained from the aqueous content of polymer shell-stabilized giant unilamellar vesicles activated (red) by a pH gradient and polymer shell-stabilized giant unilamellar vesicles without a pH gradient (black). The bioluminescence curve was calibrated by the addition of 100 nM ATP solution to assess the amount of synthesized ATP.

EXAMPLE 10

(Encapsulation of Tubulin into the Polymer Shell-Stabilized Giant Unilamellar Vesicles)

Giant unilamellar vesicles formation within polymer droplets were prepared as described in example 1. Tubulin was purified from pig brain according to previously described protocols: Castoldi, M. & Popov, A. V. Purification of brain tubulin through two cycles of polymerization-depolymerization in a high-molarity buffer. Protein Expr. Purif. 32, 83-88 (2003). It was then labeled with ATTO 488-SE (Life Technologies, Germany) as described earlier: Hyman, A. et al. Preparation of modified tubulins. Methods Enzymol 196, 478-485 (1991). Labeled and unlabeled tubulin were stored at −80° C. in PIPES storage buffer consisting of 20 mM PIPES pH 6.8, 7.25 mM $MgCl_2$, 1 mM EGTA, 1 mM 2-mercaptoethanol, 50 mM KCl, 31 mM glucose, 1 mg/ml glucose oxidase and 0.5 mg/ml catalase and 0.25 mg/ml beta-casein.

To polymerize tubulin and to form microtubule networks inside the polymer shell-stabilized giant unilamellar vesicles a two-step procedure was applied. First, polymer shell-stabilized giant unilamellar vesicles were produced as described above using a lipid mixture of DOPC:DOPS (9:1), including 1% Rhodamine B (RhB)-labeled DOPE in polymerization buffer consisting of 20 mM PIPES pH 6.8, 7.25 mM $MgCl_2$, 1 mM EGTA, 3 mM GTP, 1 mM 2-mercaptoethanol, 50 mM KCl, 31 mM glucose, 1 mg/ml glucose oxidase and 0.5 mg/ml catalase, 0.25 mg/ml beta-casein. Second, the pico-injection unit was used to inject tubulin (90% unlabeled, 10% labeled with ATTO 488 as described above) dissolved in storage buffer into these polymer shell-stabilized giant unilamellar vesicles. To achieve optimal polymerization results, the polymer shell-stabilized giant unilamellar vesicles containing tubulin were transferred to a 37° C. observation chamber.

EXAMPLE 11

(Microfluidic Release Device)

A high-throughput microfluidic device as shown in FIG. 5 was developed to release assembled lipid compartments from the stabilizing polymer droplet shells into the aqueous phase. All flows inside the device were controlled by a microfluidic flow control system (MFCS-EZ, Fluigent, France). To minimize shear forces, the height of the channels was designed to exceed the droplet diameter, and the pressure in the inlet channels was adjusted to a maximum of 20 mbar with minor corrections for individual devices and experimental conditions. The polymer shell-stabilized giant unilamellar vesicles were injected into the inlet channel of the release device and isolated at the T-junction where a tributary oil flow containing 20 vol % perfluoro-1-octanol destabilizing surfactants (Sigma-Aldrich) joins. The total flow was adjusted to allow efficient time for the destabilizing surfactants to replace and displace stabilizing surfactants prior to reaching the release unit. In this unit, the polymer shell-stabilized giant unilamellar vesicles encounter the aqueous phase in a wide perpendicular channel. To minimize the mechanical impact on the droplets at the oil/water junction, the droplets were decelerated using passive trapping structures within the microfluidic channels (i.e., rows of pillars separated by distances smaller than the representative droplets dimensions), which we designed for this purpose.

To avoid that oil penetrates into the aqueous channel whenever there weren't any droplets in the trapping structures, the aqueous flow was adjusted to achieve a zero-pressure gradient at the oil/water junction. As a result, the oil flows into the adjacent oil outlet channels without droplets blocking the slits. Whenever a droplet enters, it blocks the first slits on both sides, thereby increasing the pressure. As the droplet flows along the passive trapping structures, it passes pairs of slits, opening these up for oil flow to the oil outlet channels. With each pair of slits that opens up the channel cross section for the oil flow to the adjacent oil channels increases, subsequently decreasing the pressure that is pushing the droplet along the channel. The droplet decelerates as it approaches the oil-water interface. Upon contact with the aqueous phase, the residual surfactant layer peels off the droplet's polymer shell, which flows to the oil outlet channel. This releases the droplet's aqueous content (including the lipid compartments) into the aqueous phase.

EXAMPLE 12

The relevance of theoretically estimated lipid concentration for droplets of 100 μm diameter of 237 μM was experimentally validated. More specifically, the amount of fluorescently-labeled lipids (egg PC:egg PG, 9:1, including 0.5% ATTO 488-labelled DOPE) encapsulated into 120 μm diameter monodisperse droplets were systematically varied and their fluorescence intensity at the droplet interface were recorded.

The results are shown in FIG. 13.

In case of lipid concentrations lower than 237 μM no smaller giant unilamellar vesicles than the size of the droplet itself were observed. Instead fusion of available lipids at the inner wall of the droplet was detected. As can be observed, the lipid fluorescence intensity values are increasing approximately linearly up to the theoretical estimated concentration. At higher lipid concentrations the intensity reaches a plateau. It should be noted that at higher concentrations the excess lipids form aggregates of liposomes at the droplet interface. Inhomogeneous aggregation of liposomes on the droplet's periphery affecting precise estimation of the intensity. Therefore, higher deviation in the recorded intensity at 400 μM lipid concentration is attributed to this effect.

EXAMPLE 13

In order to evaluate if the lipid bilayer stayed intact during the release process performed as described above in connection with FIG. 5, as shown in FIG. 14 (A) oil phase (ATTO 520, yellow), (B) lipid bilayer (RhB DOPE, green), (C) encapsulated (HyLite 405, blue) and (D) continuous water phase (Alexa 647, red) were labeled with distinctive fluorophores.

FIG. 14 (E) shows a composite image of all channels.

On the bottom left of each frame is the continuous oil phase containing multiple polymer shell-stabilized giant unilamellar vesicles 36 encapsulating aqueous medium. The remainder of the frame is filled with a continuous aqueous phase 74 containing a single giant unilamellar vesicle. (A-D) The insets display a line profile intersecting the released giant unilamellar vesicle along the indicated white line for the respective fluorophore. (A) In the oil channel, no traces of remaining oil can be detected on the released giant unilamellar vesicle. (B) The fluorescent signal of the RhB DOPE is stronger compared to the polymer shell-stabilized giant unilamellar vesicle. This is likely due to reduced diffraction and refraction. (C) and (D) show no mixing between the aqueous phases was detected.

EXAMPLE 14

Furthermore, Raman spectra of droplet-stabilized giant unilamellar vesicles and of respective released giant unilamellar vesicles without polymer shell were performed.

Raman microscope was used to perform Raman spectroscopy on released giant unilamellar vesicles to provide a method for the detection of oil/surfactant residues in the released giant unilamellar vesicles. (A) shows a comparison of Raman spectra collected from the solution of surfactants in FC40 oil (brown) and from the SUVs (green), consisting of 4:4:2 of DOPC, POPC and cholesterol, respectively. Carbon-hydrogen stretching vibration of lipid tails indicated by arrow between 2800 and 3000 cm$^{-1}$.[1]

(B) shows representative Raman spectra collected through the water oil interphase of the single polymer shell-stabilized giant unilamellar vesicle as indicated by the red line in the insert bright-field image. In sake of clarity of presentation the spectra collected from the oil and water phases were brown and blue colored, respectively. (C) Representative Raman spectra collected through the water-lipid interphase of the released giant unilamellar vesicle as indicated by the red line in the insert bright-field image. In sake of clarity of presentation the spectra collected from the water phases and the lipid bilayer were blue and green colored, respectively. Importantly, no characteristic peaks of the FC40 oil/surfactant were detected within the collected spectra. Raman intensity of the carbon-hydrogen stretching vibration of lipid tails (indicated by arrow) was plotted over the screening distance.

REFERENCE NUMERALS

10 Droplet
12 Polymer shell

14 Inner space of the droplet
15 Outer space of the droplet; oil phase
16 Lipophilic perfluorinated polyether block of the copolymer forming the polymer shell
18 Hydrophilic polyether glycol block of the copolymer forming the polymer shell
20 Lipid (here in form of large unilamellar lipid-vesicles)
22 Flow-focusing microfluidic device
24 Junction
26, 26' First and second inlet channel for oil phase
28 Third inlet channel for aqueous phase
30 Outlet channel
32 Narrow orifice
34 Lipid bilayer
36 Polymer shell-stabilized giant unilamellar vesicle
38 Pico-injector device
40 Channel
42, 42' Electrode
44 Pico-injector
46 Transmembrane protein
48 Proteoliposome
50 Cytoskeleton protein
52 Filament
54 Microfluidics device
56 First inlet channel
58 Second inlet channel
60 T-junction
62 Passive trapping structure
64 Fide perpendicular channel for aqueous phase
66 Giant unilamellar vesicle without polymer shell
68, 68' Oil outlet
70 Buffer
72 Oil
74 Aqueous phase
76 Fluorinated oil
78 Drop

The invention claimed is:

1. A method for preparing a protocell in the form of a giant unilamellar vesicle, which comprises the following steps:
  a) providing a water-based droplet encapsulated by an outer polymer shell, which borders the inner space of the droplet, wherein the droplet has a maximum dimension of 0.5 µm to 1,000 µm, wherein the inner space of the droplet contains at least one lipid,
  b) transforming the lipid content of the droplet into a lipid bilayer which is arranged at and covers the inner surface of the polymer shell and oil phase in order to form a polymer shell-stabilized giant unilamellar vesicle,
  wherein said polymer shell of the droplet is formed from an amphiphilic copolymer being comprised in the oil phase,
  wherein the amphiphilic copolymer comprises at least one hydrophobic block and one hydrophilic block, wherein the at least one hydrophobic block is oriented toward the oil phase and the at least one hydrophilic block is oriented toward the aqueous phase,
  wherein in step a) a dispersion is provided, in which the droplet is dispersed in an oil-phase, wherein an aqueous phase comprising the at least one lipid is contained in the inner space of the droplet,
  wherein the at least one lipid is incorporated into the inner space of the droplet during step a) by droplet generation in a flow-focusing microfluidic device, and/or wherein the at least one lipid is incorporated into the inner space of the droplet during step a) by droplet electro-microfluidics making use of an injector,
  wherein the lipid included in the inner space of the droplet is a phospholipid, and
  wherein the lipid content of the droplet is transformed during step b) into a lipid bilayer by adjusting the concentration of ions within the inner space of the droplet and/or applying electric fields.

2. The method in accordance with claim 1, wherein the polymer shell of the droplet is made of a diblock copolymer, a triblock copolymer or a statistic copolymer.

3. The method in accordance with claim 2,
  wherein i) the polymer shell of the droplet is made of a diblock copolymer comprising a hydrophobic perfluorinated polymer block arranged at the outer side and a hydrophilic polyether glycol block arranged at the inner side of the polymer shell, or
  wherein ii) the polymer shell of the droplet is made of a triblock copolymer comprising two hydrophobic perfluorinated polymer end blocks and there between a hydrophilic polyether glycol block, wherein the triblock copolymer is folded so that the hydrophobic perfluorinated polymer blocks are arranged at the outer side and that the hydrophilic polyether glycol block is arranged at the inner side of the polymer shell, or
  wherein iii) the polymer shell of the droplet is made of a statistic copolymer consisting of a combination of a diblock copolymer comprising a hydrophobic perfluorinated polymer block arranged at the outer side and a hydrophilic polyether glycol block arranged at the inner side of the polymer shell and a triblock copolymer comprising two hydrophobic perfluorinated polymer end blocks and there between a hydrophilic polyether glycol block, wherein the triblock copolymer is folded so that the lipophilic perfluorinated polymer blocks are arranged at the outer side and that the hydrophilic polyether glycol block is arranged at the inner side of the polymer shell.

4. The method in accordance with claim 1, wherein the lipid is selected from the group consisting of phosphocholine, phosphocholine derivatives, phosphoethanolamine, phosphoethanolamine derivatives, phosphatidylcholine, phosphatidylglycerol, phosphatidylglycerol derivatives and arbitrary combinations of two or more of the aforementioned lipids.

5. The method in accordance with claim 4, wherein the lipid is selected from the group consisting of 1,2-dioleoyl-sn-glycero-3-phosphocholine, 1,2-dioleoyl-sn-glycero-3-phospho-ethanolamine, 1,2-dioleoyl-sn-glycero-3-phospho-L-serine, 1,2-dioleoyl-sn-glycero-3-[(N-(5-amino-1-carboxypentyl)iminodiacetic acid) succinyl], 1,2-dioleoyl-sn-glycero-3-phosphoethanolamine-N-(lissamine rhodamine B sulfonyl), 1-palmitoyl-2-hydroxy-sn-glycero-3-phosphate, L-α-phosphatidylcholine, L-α-phosphatidylglycerol and arbitrary combinations of two or more of the aforementioned lipids.

6. The method in accordance with claim 1, wherein the at least one lipid is incorporated into the inner space of the droplet during step a) by droplet generation in a flow-focusing microfluidic device and/or wherein the at least one lipid is incorporated into the inner space of the droplet during step a) by electro-microfluidics making use of a pico-injector.

7. The method in accordance with claim 1, wherein the at least one lipid is incorporated into the inner space of the droplet during step a) by techniques for water-in-oil emulsion formation.

8. The method in accordance with claim 1, wherein i) the at least one lipid is incorporated into the inner space of the droplet during step a) in the form of small or large unilamellar lipid-vesicles.

9. The method in accordance with claim 1, wherein the ions are magnesium ions and the concentration of magnesium ions within the inner space of the droplet is adjusted by incorporating the at least one lipid into the inner space of the droplet during step a) by droplet generation in a flow-focusing microfluidic device, wherein the lipid containing aqueous phase used therefore has a magnesium ion concentration of 1 to 100 mM.

10. The method in accordance with claim 1, wherein the ions are magnesium ions and the concentration of magnesium ions within the inner space of the droplet is adjusted during step b) by electro-microfluidics making use of an injector.

11. The method in accordance with claim 1, wherein step c) is performed by incorporating one or more proteins into the polymer shell-stabilized giant unilamellar vesicle provided in step b) by electro-microfluidics making use of an injector.

12. The method in accordance with claim 1, wherein during step c) a transmembrane protein and/or a cytoskeleton protein is incorporated into the lipid bilayer and/or into the inner space of the polymer shell-stabilized giant unilamellar vesicle.

13. The method in accordance with claim 12, wherein a protein selected from the group consisting of receptors, ATP-synthase, polymerase, actin, tubulin, antibodies, integrins, nuclei as isolated from cells and arbitrary combinations of two or more of the aforementioned proteins and nuclei and arbitrary combinations of two or more of the aforementioned proteins and nuclei are used.

14. The method in accordance with claim 1, wherein during step d) the polymer shell and the oil phase are removed from the polymer shell-stabilized giant unilamellar vesicle.

15. A protocell in the form of a polymer shell-stabilized giant unilamellar vesicle comprising a water-based droplet encapsulated by an outer polymer shell, wherein the giant unilamellar vesicle has a maximum dimension of 0.5 µm to 1,000 µm, and further comprising a lipid bilayer being composed of at least one lipid, wherein the lipid bilayer is arranged at and covers the inner surface of the polymer shell, and wherein the polymer shell of the droplet is made of an amphiphilic copolymer.

16. A protocell in the form of a giant unilamellar vesicle obtainable with a process for preparing a protocell in the form of a giant unilamellar vesicle, which comprises the following steps:
a) providing a water-based droplet encapsulated by an outer polymer shell, which borders the inner space of the droplet, wherein the droplet has a maximum dimension of 0.5 µm to 1,000 µm, wherein the inner space of the droplet contains at least one lipid,
b) transforming the lipid content of the droplet into a lipid bilayer which is arranged at and covers the inner surface of the polymer shell and oil phase in order to form a polymer shell-stabilized giant unilamellar vesicle,
c) optionally incorporating one or more proteins and/or nuclei into the polymer shell-stabilized giant unilamellar vesicle provided in step b) and
d) removing the polymer shell from the polymer shell-stabilized giant unilamellar,
wherein said polymer shell of the droplet is made of an amphiphilic copolymer,
wherein the at least one lipid is incorporated into the inner space of the droplet during step a) by droplet generation in a flow-focusing microfluidic device, and/or wherein the at least one lipid is incorporated into the inner space of the droplet during step a) by droplet electro-microfluidics making use of an injector, and
wherein the polymer shell and the oil phase are removed from the polymer shell-stabilized giant unilamellar vesicle during step d) by a microfluidic device or by a bulk technique by adding destabilizing molecules.

17. The method in accordance with claim 1, further comprising step of
c) incorporating one or more proteins and/or nuclei into the polymer shell-stabilized giant unilamellar vesicle provided in step b).

18. The method in accordance with claim 1, further comprising step of
d) removing the polymer shell from the polymer shell-stabilized giant unilamellar vesicle,
wherein the polymer shell and the oil phase are removed from the polymer shell-stabilized giant unilamellar vesicle during step d) by a microfluidic device or by a bulk technique by adding destabilizing molecules.

* * * * *